(12) United States Patent
Beliveau et al.

(10) Patent No.: US 7,862,809 B2
(45) Date of Patent: Jan. 4, 2011

(54) USE OF STRAINS OF LACTOBACILLUS AND BY-PRODUCTS THEREOF FOR INHIBITING FORMATION OF BLOOD VESSELS

(75) Inventors: Richard Beliveau, Ile-des-soeurs (CA); Francois-Marie Luquet, Orsay (FR)

(73) Assignee: Bio-K Plus International, Inc., Laval, Quebec (CA)

( * ) Notice: Subject to any disclaimer, the term of this patent is extended or adjusted under 35 U.S.C. 154(b) by 805 days.

(21) Appl. No.: 10/595,819

(22) PCT Filed: Nov. 15, 2004

(86) PCT No.: PCT/CA2004/001968

§ 371 (c)(1), (2), (4) Date: Nov. 30, 2006

(87) PCT Pub. No.: WO2005/046703

PCT Pub. Date: May 26, 2005

(65) Prior Publication Data

US 2007/0086991 A1 Apr. 19, 2007

(30) Foreign Application Priority Data

Nov. 13, 2003 (CA) .................................... 2448643

(51) Int. Cl.
*C12N 1/20* (2006.01)
*A01N 61/00* (2006.01)
(52) U.S. Cl. ................. 424/93.45; 435/252.9
(58) Field of Classification Search ........................ None
See application file for complete search history.

(56) References Cited

U.S. PATENT DOCUMENTS 6,491,956 B2 * 12/2002 Heo et al. .................... 426/71
6,596,530 B1 * 7/2003 Kimura et al. .............. 435/252.9

FOREIGN PATENT DOCUMENTS

| WO | WO03045405 | 6/2003 |
|---|---|---|
| WO | 2004069178 | 8/2006 |

OTHER PUBLICATIONS

Konturek et al. Regulatory Peptides. 2000, vol. 93, No. 1-3, pp. 13-19.*
Arimochi, H. et al., Biochem Biophys Res Commun 1997, vol. 238 No. 3, pp. 753-757.
Baharav, E. et al., J. Nutr, Aug. 2004, vol. 134, No. 8, pp. 1964-1919.
Griffioen, A.W. et al., Pharmacol Rev, 2000, vol. 52, No. 2, pp. 237-226.
Hirayama, K., et al., Microbes and Infection 2, 2000, vol. 2, No. 6, pp. 681-686.
Kato, I. et al., Life Sci. 1998, vol. 63, No. 8, pp. 635-644.
Matsuzaki, T. Int J Food Microbiol. 1998, vol. 41, No. 2, pp. 133-140.
Mital, B.K., et al., Crit Rev Microbiol. 1995, vol. 21, No. 3, pp. 175-214.

* cited by examiner

*Primary Examiner*—Vera Afremova
(74) *Attorney, Agent, or Firm*—Milbank, Tweed, Hadley & McCloy LLP

(57) ABSTRACT

A lactic composition containing at least a bacterial strain selected from the group consisting of *Lactobacillus acidophilus*, *Lactobacillus casei* and a mixture of *Lactobacillus acidophilus* and *Lactobacillus casei*, and a whole broth of the bacterial strain or the mixture of the bacterial strains, is useful for the prevention or treatment of disorders which are angiogenesis dependant. Both the lactic composition and its supernatant can be used for prevention or treatment of angiogenesis dependant disorders. The supernatant of the lactic composition exhibits antiangiogenic properties.

5 Claims, 36 Drawing Sheets

Effect of different supernatants of lactic acid bacteria on the formation of capillary structures by HUVEC cells 1. Supernatant of lactic acid bacteria
2. Concentrated supernatant of lactic acid bacteria (molecules > 5 000 kDa)
3. Filtrate of lactic acid bacteria (molecules ≤ à 5 000 kDa)

Effect of different supernatants of lactic acid bacteria on the formation of capillary structure by HUVEC cells 1. Supernatant of lactic acid bacteria
2. Concentrated supernatant of lactic acid bacteria (molecules > 5 000 kDa)
3. Filtrate of lactic acid bacteria (molecules ≤ à 5 000 kDa)

Effect of different BIO-K PLUS supernatants on the formation of the capillary structure by HUVEC cells 1. Supernatant of BIO-K PLUS (with milk product)
2. Supernatant of BIO-K PLUS (without milk product)
3. Supernatant of BIO-K PLUS (with milk product) pH7.2
4. Supernatant of BIO-K PLUS (without milk product) pH7.2

Effect of different BIO-K PLUS supernatants on the formation of the capillary structure by HUVEC cells 1. Supernatant of BIO-K PLUS (with milk product)
2. Supernatant of BIO-K PLUS (without milk product)
3. Supernatant of BIO-K PLUS (with milk product) pH7.2
4. Supernatant of BIO-K PLUS (without milk product) pH7.2

Effect of lactic acid bacteria supernatant on the migration of BAEC cells

1. Supernatant of lactic acid bacteria
2. Concentrated supernatant of lactic acid bacteria (molecules > 5 000 kDa)
3. Filtrate of lactic acid bacteria (molecules ≤ à 5 000 kDa)

Effect of BIO-K PLUS supernatant on the migration of BAEC cells

1. BIO-K PLUS supernatant (with milk product)
2. BIO-K PLUS supernatant (without milk product)

Effect of lactic acid bacteria supernatant on migration of HUVEC cells

1. Supernatant of lactic acid bacteria
2. Concentrated supernatant of lactic acid bacteria (molecules > 5 000 kDa)
3. Filtrate of lactic acid bacteria (molecules ≤ à 5 000 kDa)

Effect of BIO-K PLUS supernatant on migration of HUVEC cells

1. Supernatant of BIO-K PLUS (with milk product)
2. Supernatant of BIO-K PLUS (without milk product)

Effect of BIO-K PLUS supernatant (with milk product) on migration of BAEC cells

Effect of BIO-K PLUS supernatant (without milk product) on migration of BAEC cells Effect of BIO-K PLUS supernatant (with milk product) on HUVEC cells proliferation Effect of BIO-K PLUS supernatant (without milk product) on HUVEC cells proliferation Effect of BIO-K PLUS supernatant (with milk product) on the proliferation of HUVEC cells induced by bFGF Effect of BIO-K PLUS supernatant (without milk product) on the proliferation of HUVEC cells induced by bFGF

Effect of the supernatants of the lactic bacteria on the tube formation by endothelial cells (n = 1)

A. HUVECs

Effect of the supernatants of the lactic bacteria on the tube formation by endothelial cells (n = 2)

Effect of different supernatants of BIOK PLUS on the formation of capillary structures by endothelial cells (HUVEC)

USE OF STRAINS OF LACTOBACILLUS AND BY-PRODUCTS THEREOF FOR INHIBITING FORMATION OF BLOOD VESSELS

FIELD OF THE INVENTION

The present invention is related to the field of probiotics useful in the prevention of disorders.

BRIEF DESCRIPTION OF THE PRIOR ART

Cancer research aims to discover means by which the aggressive growth of solid tumours and their metastases can be abolished in a specific way without causing treatment resistance, or provoke excessive toxicity in treated patients. The challenge is high, since the transformation of normal cells into tumour cells is associated with the acquisition of resistance to most cytotoxic agents presently used in therapy. Several studies done in the last few years have demonstrated that tumour cells do not represent the only factor responsible for tumour growth. Blood vessels present within these tumours play also a crucial role. It has been clearly established that blood vessels, formed by the angiogenesis process (FIGS. 15 and 16), are essential to aggressive growth of tumours and their metastases. This angiogenesis is due to the capacity of tumour cells to secrete a certain number of angiogenic factors, like vascular endothelium growth factor (VEGF) and fibroblastic growth factor (FGF), linking with high affinity the surface of endothelial cells. The stimulation of endothelial cells by these factors, results not only in an increase of secretion of enzymes degrading the extra cellular matrix components, but also in the stimulation of the migration and the proliferation of these cells. The thus stimulated cells invade the matrix surrounding the tumours, forming a capillary network which will ensure the growth of tumour cells, by giving them nutrients and oxygen necessary for their development. The inhibition of blood contribution to the tumours constitutes thus a target of choice for the development of new therapeutic anticancerous approaches targeting specifically angiogenesis to limit or eliminate tumour progression.

It is estimated that life habits and eating habits are responsible for more that one third of new diagnosed cancers. Consequently, prevention (Nutra-prevention) presently creates a big interest and it is estimated that in the following few years, it will bring reduction in mortality rate related to cancer more than those attained with the available treatments.

Accordingly, there is a need for a nutraceutical product that would have antiangiogenetic characteristics.

SUMMARY OF THE INVENTION

An object of the present invention is to provide a product that satisfies the above-mentioned need.

The present invention concerns a lactic composition comprising at least a bacterial strain selected from the group consisting of *Lactobacillus acidophilus, Lactobacillus casei* and a mixture thereof, and a whole broth of each of said bacterial strain or a mixture thereof, characterized in that the lactic composition is useful in the prevention or the treatment of angiogenesis dependant disorders.

The present invention also concerns the supernatant of the lactic composition according to the invention. The supernatant exhibits antiangiogenic properties.

The present invention also concerns the method of obtaining the supernatant according to the invention. The method comprises the steps of:

a) suspension of at least one lactic acid bacteria strain selected from the group consisting of *Lactobacillus acidophilus* and *Lactobacillus casei* in complex medium to get a suspension
b) incubation of the suspension;
c) dilution of the suspension in a complex medium;
d) incubation,
e) centrifugation to obtain an liquid; and
f) filtration of the liquid obtained to obtain the supernatant The present invention also concerns the use of the supernatant or the composition according to the invention in the prevention or the treatment of an angiogenesis dependent disorder in a mammal.

Moreover, the present invention concerns a method for prevention or treatment of angiogenesis dependant disorders in a mammal. The method of treatment or prevention comprises the step of administering to the mammal an effective amount of the lactic composition or the supernatant according to the invention.

An advantage of the present invention is that it provides for a method of prevention of angiogenesis dependant disorders, thus greatly reducing or eliminating the risk of occurrence of such disorders.

Another advantage of the present invention is that it provides for prevention or treatment of angiogenesis dependant disorders which is not toxic.

A third advantage of the present invention is that it provides for a non-invasive method of prevention or treatment of angiogenesis dependant disorders.

Another advantage of the present invention is also that it provides for a method prevention or treatment of angiogenesis dependant disorders which presents little or no side effects.

Yet another advantage of the present invention is that it provides for a composition or a supernatant that can be used over a prolonged period of time, with little or no side effects. Such composition or supernatant are readily available in health food stores or specialized markets without the need for a prescription.

Other objects and advantages of the present invention will be apparent upon reading the following non-restrictive detailed description, made with reference to the accompanying drawings

DETAILED DESCRIPTION OF THE INVENTION

Figure 1A:
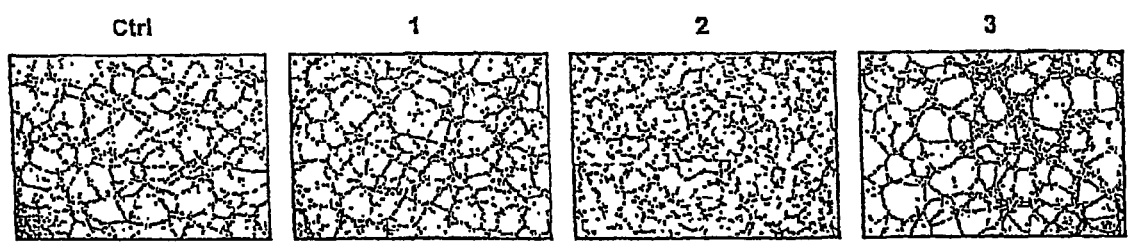
FIGS. 1A and 1B show the effect of different supernatants of lactic acid bacteria on the formation of capillary structures by HUVEC cells.
Figure 1A:
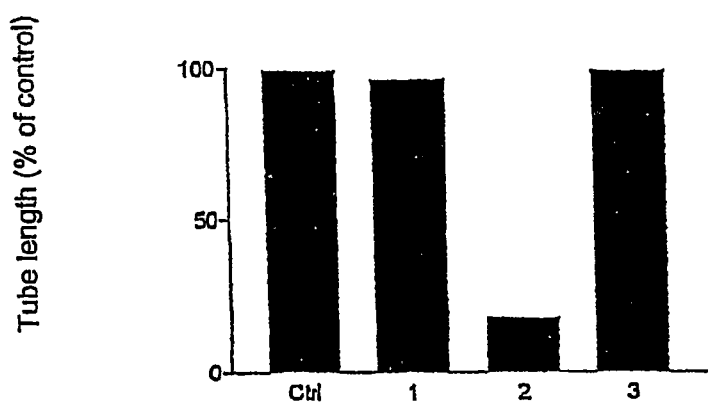

In order to provide an even clearer and more consistent understanding of the description, including the scope given herein to such terms, the following definitions are provided:

By "mammal", it is meant any living organism which may be subject to disorders that are angiogenesis-dependant such as tumour growth, and this includes vertebrate beings such as in particular human beings and domestic and wild animals.

By "treat", it is meant a process by which the symptoms of angiogenesis-dependant disorders, and particularly tumour growth, are maintained at a constant level, reduced or completely eliminated.

By "prevent", it is meant a process by which the angiogenesis-dependant disorders such as tumour growth are controlled or delayed.

By "nutritionally acceptable", it is meant a vehicle that can be administered without risk to a mammal, in particular to a human, and this with little or no negative or toxic side effects. Such a vehicle can be used for different functions. For example, it can be used as a preservation, solubilizing, stabilizing, emulsifying, softening, coloring, odoring agent, or as an antioxidant agent. These types of vehicles may be easily prepared by using methods well known by a person in the art.

By "broth", it is meant a medium containing a variety of nutrients which is used to grow cultures of bacteria and other micro-organisms. Broth can also be the liquid in which the micro-organisms of the composition according to the invention are found.

By "supernatant", it is meant the soluble liquid fraction of a sample after centrifugation or precipitation of insoluble solids and more specifically of the bacterial strains according to the present invention. The supernatant of the present invention comprises molecules secreted by the bacterial strains of the invention. The secreted molecules have a potential antiangiogenic property.

The inventors have discovered that a lactic composition comprising at least a bacterial strain selected from the group consisting of *Lactobacillus acidophilus, Lactobacillus casei* and a mixture thereof, and a whole broth of each of said bacterial strain or a mixture thereof, is useful in the prevention or the treatment of angiogenesis dependant disorders.

In a preferred embodiment of the invention, the lactic composition comprises at least *Lactobacillus acidophilus* strain I-1492 deposited at the CNCM.

The composition according to the present invention can be presented in any solid or liquid form that is usual to nutritional administration, that is for example for liquid administration forms, in a gel, or any other support known by a person skilled in the art. Among the compositions that are used, we can in particular cite compositions that can be administered orally. The composition can also be administered in the form of food or food supplements.

A person versed in the art will know how to prepare compositions that are nutritionally acceptable and determine, in function of many factors, the privileged method of administration and the quantity that should be administered. Among the factors that can influence his choices we find: the exact nature of the ingredients, active or not, entering in the composition; the condition, the age and the weight of the mammal, the stage of the angiogenesis dependant disorder and the nature of the treatment.

The lactic composition of the invention comprises, according yet to another preferred embodiment, at least 500 millions per gram of a population of living and active micro-organisms of the *Lactobacillus acidophilus* strains after 90 days under refrigeration, where at least 380 millions per gram are micro-organisms of the *Lactobacillus acidophilus* CNCM I-1492 strain. According to another preferred embodiment of the invention, the composition comprises the Bio-K Plus™ products. According to yet another preferred embodiment of the invention, the lactic composition of the invention further comprises fermented milk proteins and fermented soy proteins. Bio-K Plus™ products are lactic ferment products readily available on the market and sold by the company Bio-K Plus International Inc. The Bio-K Plus™ products contains *Lactobacillus acidophilus* and *Lactobacillus casei*, and more specifically *Lactobacillus acidophilus* I-1492 CNCM.

The present invention is also related to the supernatant of the lactic composition of the present invention. The supernatant exhibits antiangiogenic properties.

The supernatant of the invention is obtained by a method that comprises the steps of:
  a) suspension of at least one lactic acid bacteria strain selected from the group consisting of *Lactobacillus acidophilus* and *Lactobacillus casei* in complex medium to get a suspension;
  b) incubation of the suspension;

c) dilution of the suspension in a complex medium;
d) incubation;
e) centrifugation to obtain an liquid; and
f) filtration of the liquid obtained to obtain the supernatant.

In a preferred embodiment of the invention, the complex medium of steps a) and c) is MRS medium. In another preferred embodiment of the invention, the incubation of step d) is done at 37° C. In yet another preferred embodiment of the invention, the centrifugation is done at 1000×g for 15 min. In a preferred embodiment of the invention, the filtration is preferably done with a 0.45 µm filter then with a 0.22 µm filter.

In a preferred embodiment of the invention, the method further comprises the steps of:

g) adding the supernatant of step f to Ultrafree-4™ tubes;
h) centrifugation to obtain two layers;
i) separation of the two layers into two separate Eppendorf™ tube.

The centrifugation of step h) is preferably done at 3000×g for 30 min.

Hence, in a preferred embodiment of the invention, the supernatant is concentrated and more preferably 10× concentrated. In another preferred embodiment of the invention, the supernatant comprises molecules of a size larger than 5000 kDa.

In another preferred embodiment of the invention, the bacteria of the composition are irradiated or non-irradiated. In yet another preferred embodiment, the bacteria are irradiated at 3 kGy, 6 kGy or 9 kGy. In a preferred embodiment of the invention, the supernatant is obtained by centrifuging twice the irradiated bacteria. In a preferred embodiment, the first centrifugation is done at 6000 g for 15 min at 4° C. and the second centrifugation is done at 10000 g for 20 min also at 4° C. In a preferred embodiment of the invention, the supernatant is sterile and bacteria free.

The present invention is also related to the lactic composition and the supernatant as antiangiogenic.

The lactic composition or the supernatant according to the invention is used in the prevention or the treatment of an angiogenesis dependant disorder in a mammal and more preferably in a human. In a preferred embodiment of the invention, examples of such disorders are retinopathy, infantile haemangioma, rheumatoid arthritis, psoriasis, duodenal ulcers, post-angioplasty restenosis and tumour growth. In a more preferred embodiment of the invention the lactic composition or the supernatant according to the invention is used in the prevention or the treatment of tumour growth.

The invention also concerns the method of preventing and treating of angiogenesis dependant disorders such as the disorders mentioned above, by administration of the lactic composition or of the supernatant of the invention to a mammal and more preferably to a human. In a more preferred embodiment, the invention concerns the method of preventing and treating tumour growth. According to a preferred embodiment of the invention, the mentioned administration of the composition or the supernatant is an oral administration.

A therapeutically effective quantity of lactic composition is the quantity necessary to obtain positive results without causing excessively negative side effects in the host to which the lactic composition is administered. Moreover, an efficient quantity of lactic composition to treat a particular angiogenesis dependant disorder is a quantity that is sufficient to attenuate or to reduce In any fashion the symptoms linked to an angiogenesis dependant disorder. Such a quantity can be administered in a single dose or can be administered according to a regime, by which it is efficient. The quantity of lactic composition according to the present invention can treat the angiogenesis dependant disorder but, typically, it is administered in order to attenuate the symptoms of angiogenesis dependant disorder. The exact quantity of lactic composition or each of the components of the composition to be administered will vary according to factors such as the type of angiogenesis dependant disorder to be treated, the other ingredients in the composition, the method of administration, the age and the weight of the mammal.

The present invention also concerns useful pharmaceutical kits, for example, for the prevention or the treatment of an angiogenesis dependant disorder such as tumour growth. The kits comprise one or many containers further containing a composition according to the present invention. Such kits can also include, if desired, one or many conventional pharmaceutical components like, for example, containers containing one or many pharmaceutically acceptable vehicles, or any other additional component, which will be obvious to a person skilled in the art. A kit according to the present invention can advantageously include instructions in pamphlet form or on any other printed support, indicating the quantities of the components to be administered, the instructions for administration, and/or the instructions to mix the components.

Other objects and advantages of the present invention will be apparent upon reading the following non-restrictive description of several preferred embodiments and the accompanying examples.

The example herein after will allow highlighting other characteristics and advantages of the present invention.

Examples

The following examples are illustrative of the applicability of the present invention and are not intended to limit its scope. Modifications and variations can be made therein without departing from the spirit and scope of the invention. Although any method and material similar or equivalent to those described herein can be used in the practice for testing of the present invention, the preferred methods and materials are described. The following experimental procedures and materials were used for the examples set fort below Effects of Several Supernatants of Bio-K-Plus Lactic Acid Bacteria on Endothelial Cells Lines Experimental Approach Used 1. Effect on the blood capillary network formation;
2. Effect on the endothelial cells migration through blood vessel toward a tumour;
3. Effect of endothelial cells proliferation towards the tumour.

The following examples are focused on the characterisation of the antiangiogenic properties of lactic acid bacteria composing the food products of BIO-K-Plus on endothelial cells of human umbilical cord (HUVECs) and endothelial cells of bovine aorta (BAECs).

1.0 Preparation of Study Material

In the present study, the inventors have characterized the action of diverse supernatants coming from lactic acid bacteria (medium secreted by bacteria) and from BIO-K-Plus food products.

1.1 Lactic Acid Bacteria Supernatants

The bacteria have been received in 9 ml of a complex MRS medium (Difco Laboratories, Detroit, USA) and 100 µl of this suspension has been multiplied in 100 ml of the same medium. After 18 hours of incubation at 37° C. (agitation at a speed of 250 RPM), aliquots of 1.2 ml have been taken and distributed in sterile eppendorf tubes to which 0.4 ml of 80% glycerol had been previously added. The eppendorf tubes were then frozen at −80° C.

In order to obtain the lactic acid bacteria supernatants, a 100 µl of the bacterial suspension coming from a frozen tube has been taken and this suspension has been multiplied in a 100 ml of MRS medium (Difco Laboratories, Detroit, USA) (according to the same procedure described above). After 18 hours of incubation, a reculture has been done: 1 ml of bacterial suspension in 100 ml of MRS medium (Difco Laboratories, Detroit, USA) (1/100 dilution). This medium has been incubated at 37° C. until the log growth phase has been reached corresponding to a density 0.5 at $A_{600}$. Then, the supernatant has been obtained by centrifugation (1000×g. 15 min) and filtered twice (a filter of 0.45 µm followed by a filter of 0.22 µm). A portion of the supernatant has been aliquoted into sterile eppendorf tubes and frozen at −80° C. The other portion of the supernatant has been concentrated 10× with Ultrafree-4™ tubes (>5 000 kDa) by centrifugation (3 000×g. 30 min). Then, two types of supernatants were obtained: one supernatant 10× concentrated containing molecules bigger than 5 000 kDa and one filtrate containing molecules that are smaller than 5 000 kDa. Following this, the supernatants have been aliquoted and frozen at −80° C.

1.2 BIO-K-Plus Food Products Supernatants

In the present study, the supernatants have been obtained in two types of BIO-K-Plus™ food products: a compound with milk product (fermented milk proteins) and a compound without milk product (fermented soy proteins). The supernatants of these products have been obtained following two centrifugations (one at 6 000×g, 15 min, 4° C. and the other at 20 000 RPM, 30 min. 4° C.). Afterwards, they have been filtered on two filters (a filter of 0.45 µm followed by a filter of 0.22 µm) in order to obtain supernatants without bacteria and sterile for endothelial cell lines treatment. Supernatants have been frozen at −80° C. until use.

2.0 Results 2.1 In Vitro Characterization of Lactic Acid Bacteria Supernatants and BIO-K-Plus™ Food Products Supernatants on the Formation of Capillary Structures by HUVECs.

Figure 1B:
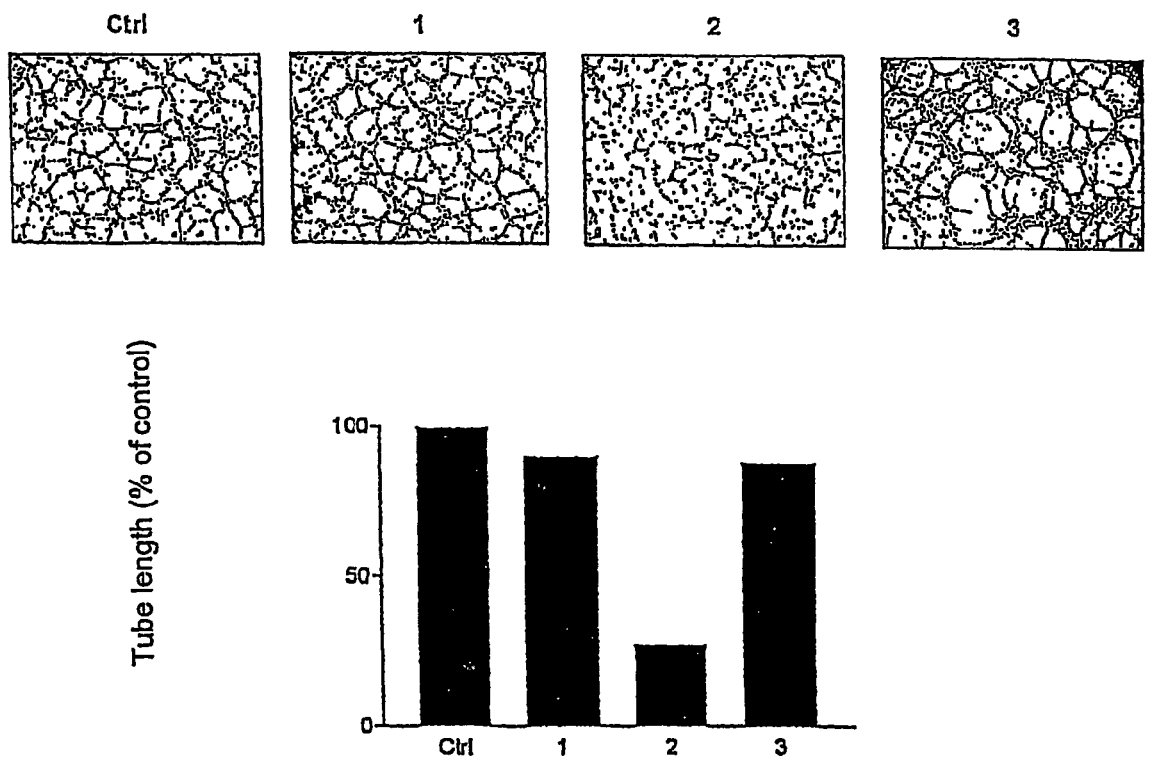

First, the inventors have verified if the supernatants of lactic acid bacteria disturb the formation of capillary structures on Matrigel by HUVECs. The cells have been cultured on a matrix containing a heterogeneous mix of growth factors (bFGF, TGF-β, VEGF, HGF) as well as several proteins of the extra cellular matrix (collagen, laminin, and fibrin) and proteases (MMPs, uPA, tPA), artificially recreating the matrix support found in vivo. A six hours incubation in presence of different supernatants (1/4 dilution) at 37° C. has permitted to observe an inhibitory effect (varying from 18.2% to 27.5% inhibition; n=2) of 10× concentrated lactic acid bacteria supernatants (FIGS. 1A, 1B). Moreover, it was observed that the formed networks are incomplete and not structured when compared to the control.

Figure 2A:
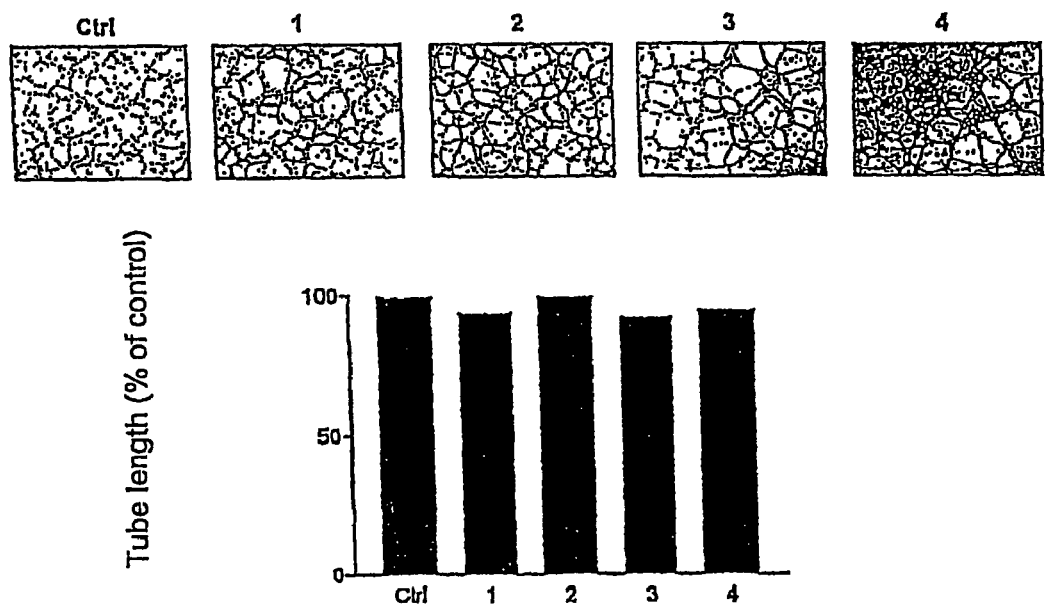
FIGS. 2A and 2B show the effect of different Bio-K Plus™ supernatants on the formation of capillary structure by HUVEC cells.
Figure 2B:
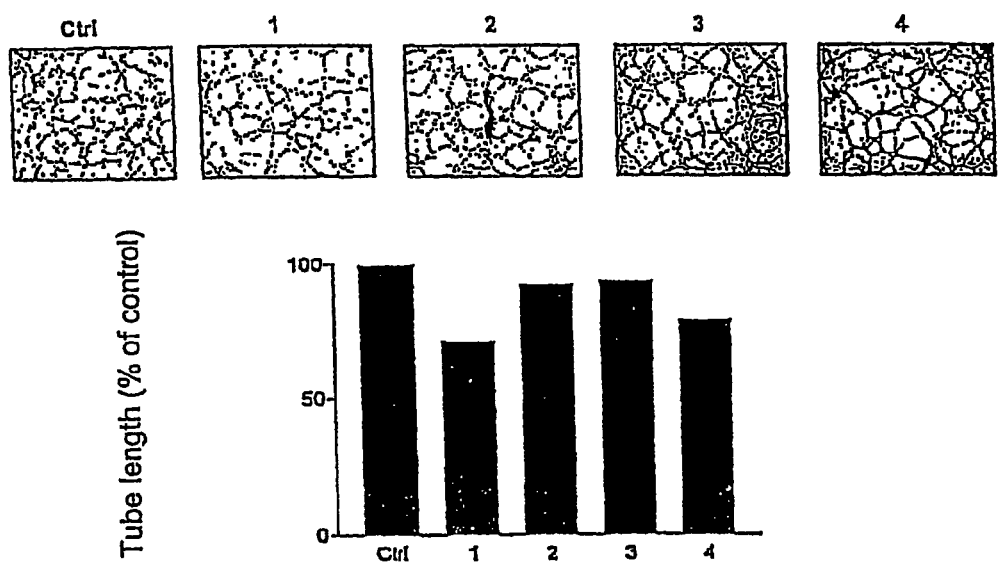

Second, the inventors have verified if BIO-K-Plush™ supernatants disturb also the formation of structures by HUVECs (FIGS. 2A, 2B). The results seem to demonstrate that their effects are not significant. Moreover, it was noted that the pH of the BIO-K-Plus™ supernatants does not seem to affect the network formation.

2.2 In Vitro Characterisation of Lactic Acid Bacteria Supernatants and BIO-K-Plus™ Food Products Supernatants on the Migratory Potential of BAECs and HUVECs.

Endothelial cells migration has been measured by Boyden type culture chambers (FIG. 1B). These are two chambers containing 6.5 mm wells separated by a polycarbonate membrane having 8.0 µm and previously smeared with gelatin. This membrane constitutes an artificial barrier. The growing endothelial cells were harvested with trypsin, counted, centrifuged and re-suspended at a density of $1.0 \times 10^8$ cells per ml in an appropriate migration buffer. The cells have been added to the wells of the upper part of the membrane and incubated at 37° C. After 30 min adhesion, different supernatants have been added to the upper and lower wells of the chamber. After 2 hours, the VEGF has been added as a chemo attractant in the lower wells. After 3 hours, the cells present at the internal surface of the membrane, thus those that have invaded the barrier, were fixed, stained and counted with the high-resolution microscope. The inhibitory activity of each of the supernatants has been analysed in function of the presence or absence of VEGF.

Figure 3A:
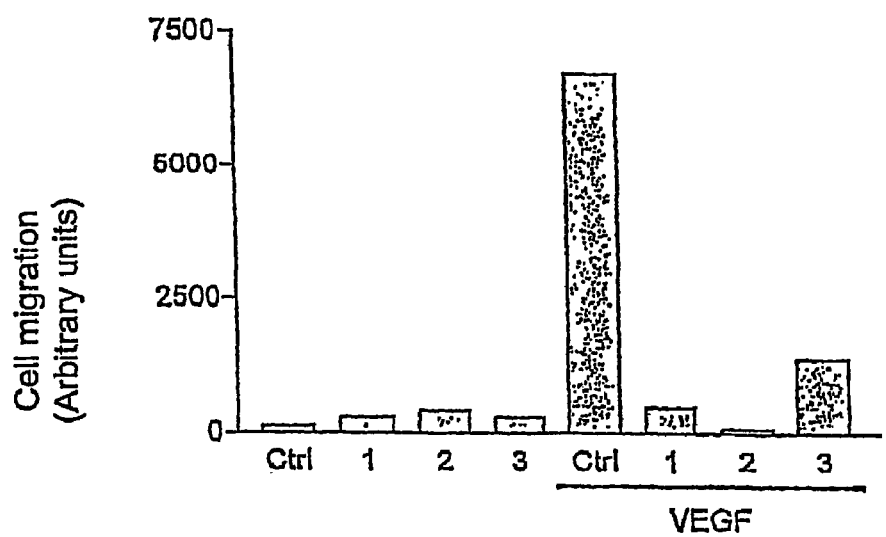
FIG. 3A shows the effect of lactic acid bacteria supernatant on the migration of BAEC cells.
Figure 3B:
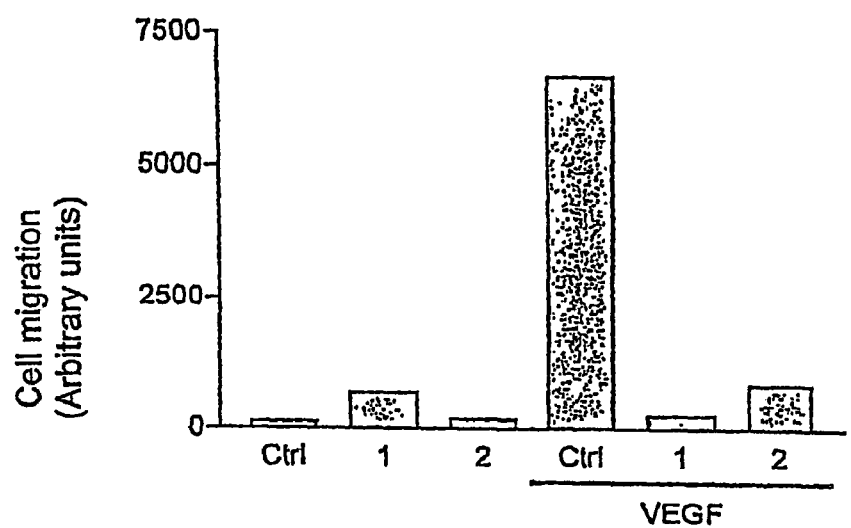
FIG. 3B shows the effect of Bio-K Plus™ supernatant on the migration of BAEC cells.
Figure 4A:
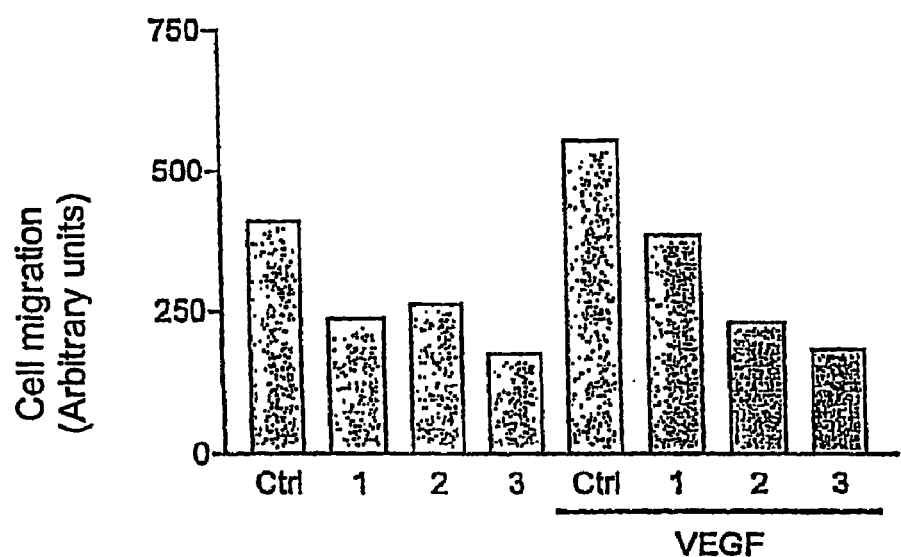
FIG. 4A shows the effect of lactic acid bacteria supernatant on migration of HUVEC cells.
Figure 4B:
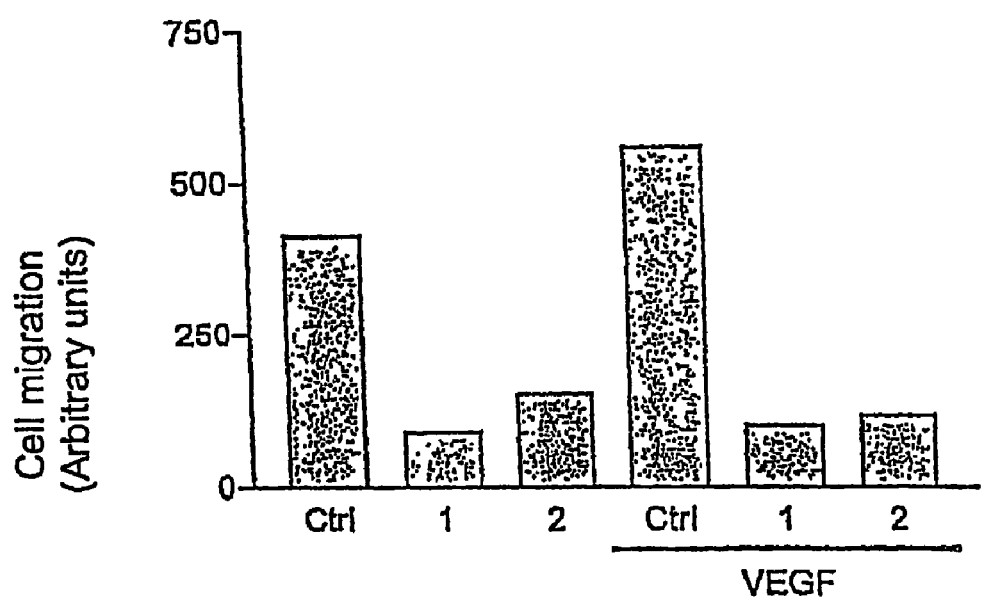
FIG. 4B shows the effect of Bio-K Plus™ supernatant on migration of HUVEC cells.

First, a dilution of 1/4 of each of the supernatants to be tested in the appropriate cellular culture medium has been used in order to determine which supernatant has a potential effect on migration. The results in BAECs demonstrate that all supernatants have an inhibitory effect on the stimulation of the migration induced by VEGF (FIGS. 3A, 3B). Moreover, it was noted that for the lactic acid bacteria concentrated supernatants, the inhibition is complete. Concerning the HUVECs, all supernatants inhibit the stimulation induced by VEGF, as well as the basal migration level (FIGS. 4A, 4B). The inhibitor effect seems more important for the BIO-K-Plus™supernatants (FIG. 4B).

Figure 5A:
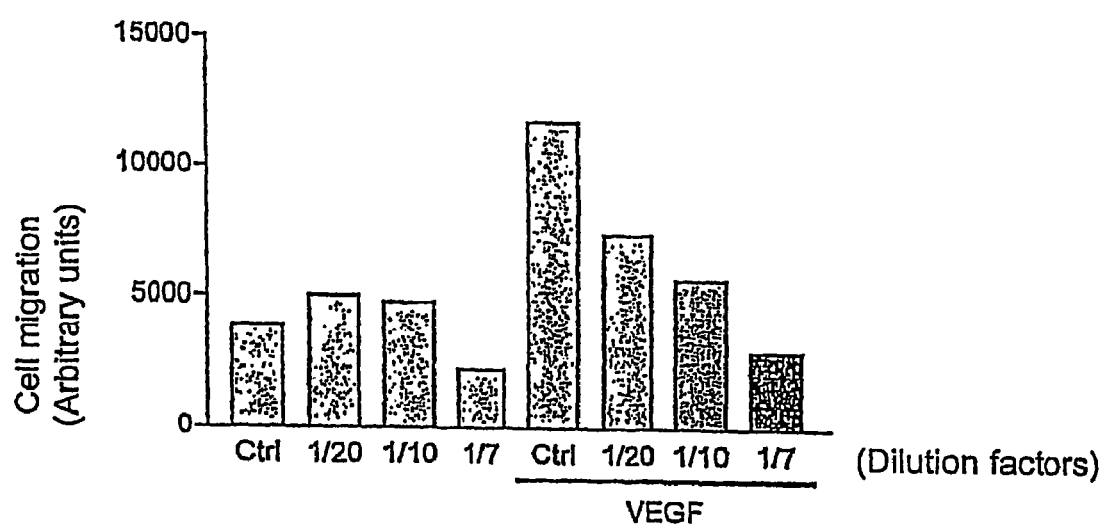
FIG. 5A shows the effect of Bio-K Plus™ supernatant (with milk product) on migration of BAEC cells.
Figure 5B:
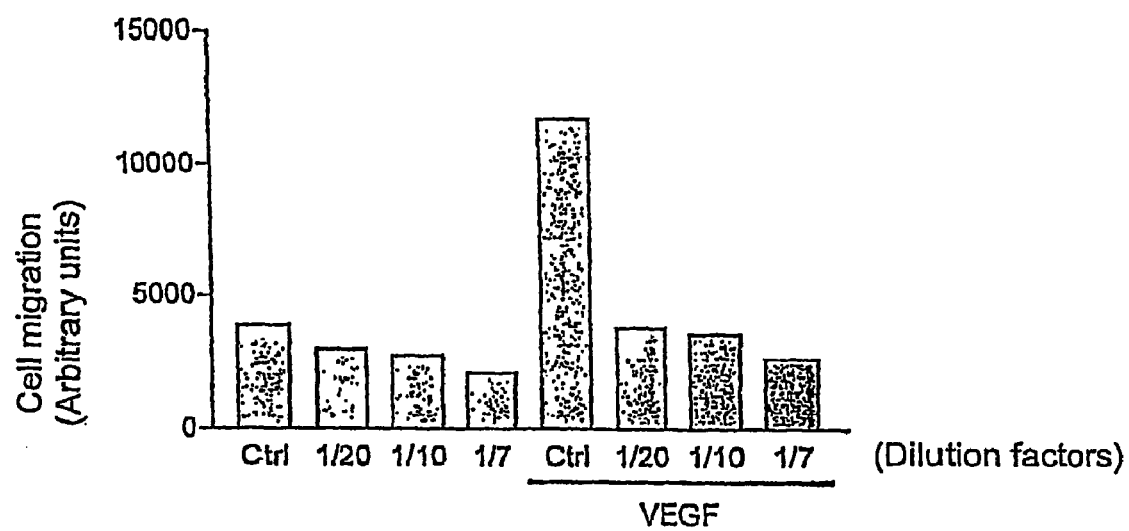
FIG. 5B shows the effect of Bio-K Plus™ supernatant (without milk product) on migration of BAEC cells.

Following, details of the inhibitor effect of supernatants in function of their dilution have been further analysed. The obtained results on the BIO-K-Plus™ supernatants (with milk product) seem to demonstrate that inhibitor effect on the stimulation induced by VEGF is function of dilution and that the weakest dilution (1/7) has also an inhibitor effect on the basal level of migration (FIG. 5A). Similar results have been obtained on BIO-K-Plus™ supernatants (without milk product) (FIG. 5B). The inventors noted however that the BAECs cells migration seem more sensitive to 1/20 and 1/10 dilutions, especially on the basal level.

2.3—In Vitro Characterisation of BIO-K-Plus™ Food Products Supernatants on HUVECs Proliferation The test used to study cell proliferation is WST-1, a technique which measures mitochondrial activity of cells. For that purpose, HUVECs have been cultured in 96 wells plate at a density of 4 000 cells/well. After 24 hours incubation, the different supernatants have been added separately in each well. After 30 min of incubation, the bFGF has been added. A solution of WST-1 of a Boehringer kit has been added in each well after different incubation times (0 h, 24 h, 48 h and 72 h) and metabolic activity has been quantified at 450 nm. Inhibitory activity of each of the supernatants has been analyzed in function of presence or absence of bFGF.

Figure 6A:
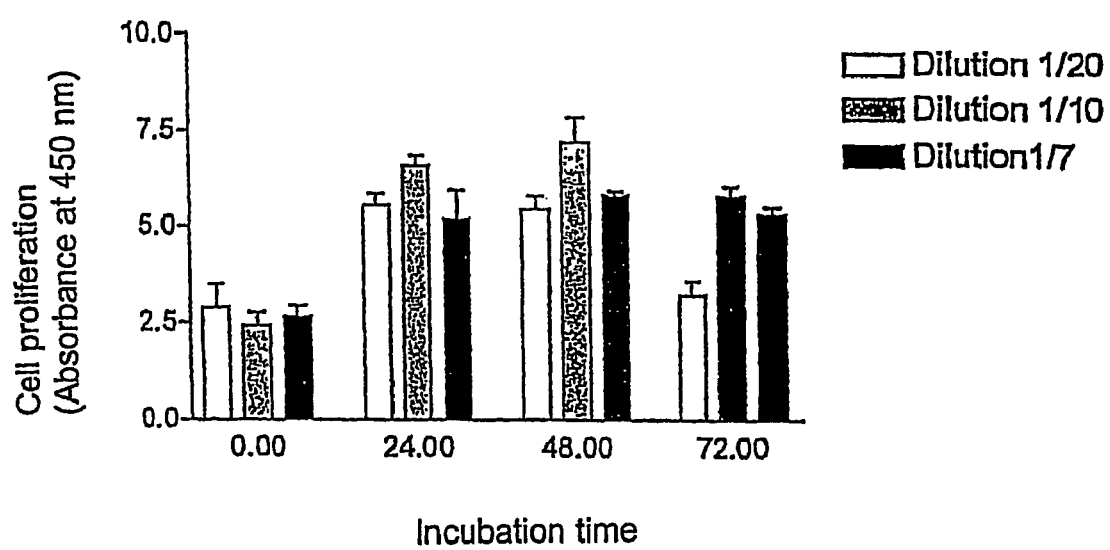
FIG. 6A shows the effect of Bio-K Plus™ supernatant (with milk product) on HUVEC cells proliferation.
Figure 6B:
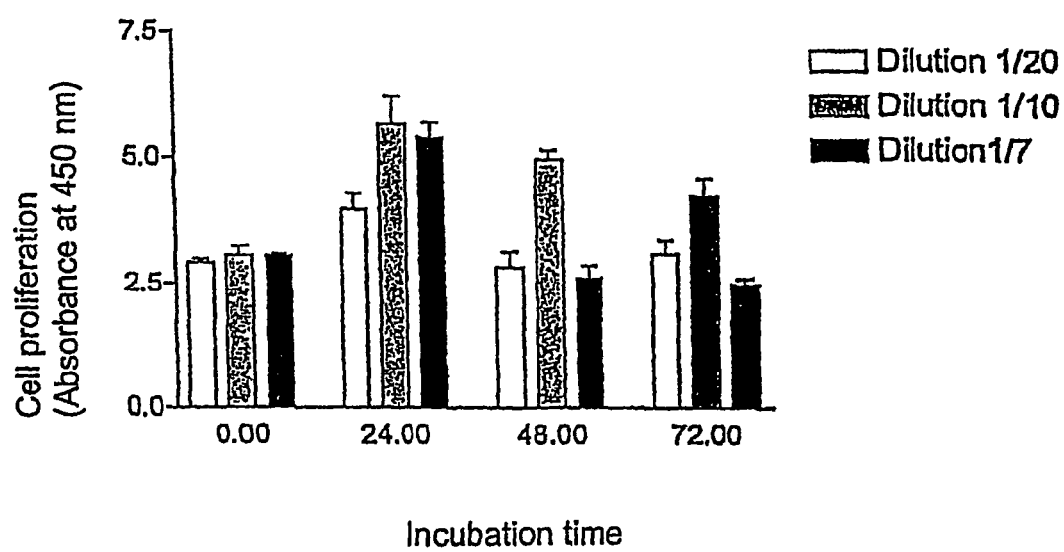
FIG. 6B shows the effect of Bio-K Plus™ supernatant (without milk product) on HUVEC cells proliferation.
Figure 7A:
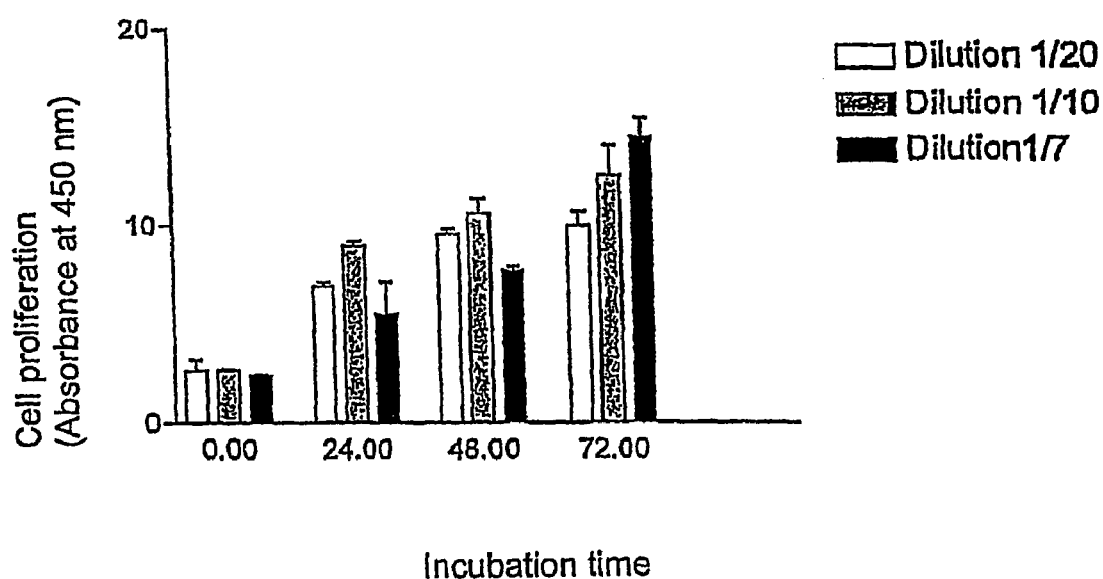
FIG. 7A shows the effect of Bio-K Plus™ supernatant (with milk product) on the proliferation of HUVEC cells induced by bFGF.
Figure 7B:
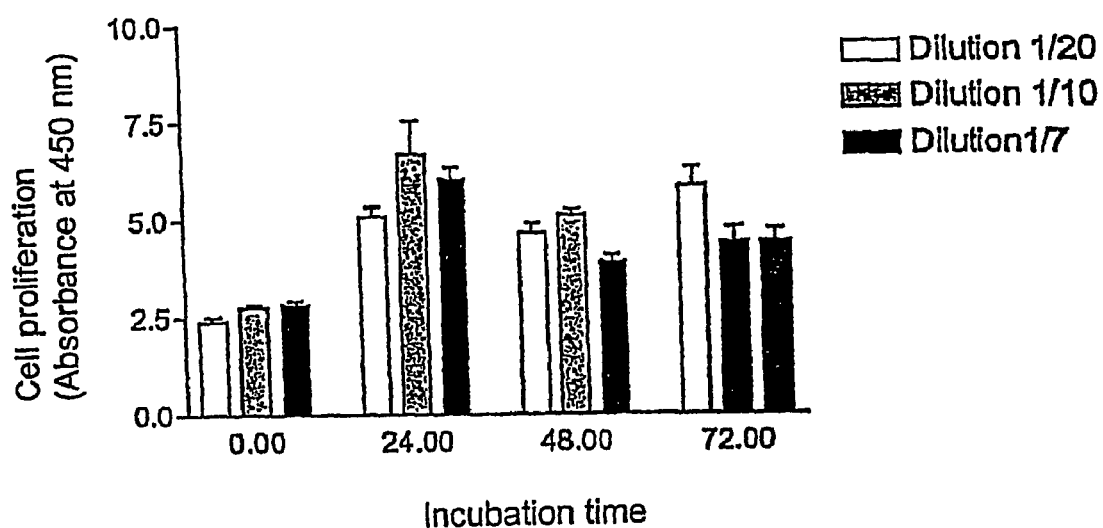
FIG. 7B shows the effect of Bio-K Plus™ supernatant (without milk product) on the proliferation of HUVEC cells induced by bFGF.

The different supernatants of BIO-K-Plus™ do not seem to inhibit the proliferation of HUVECs at 0 (FIGS. 6A, 6B). Moreover, if the effect of different dilutions of BIO-K-Plus™ supernatants (with milk product) and BIO-K-Plus™ (without milk product) are compared, in absence (FIGS. 6A, 6B) and in presence of bFGF (FIGS. 7A, 7B), one notes that the cells proliferation is increased in presence of the growth factor, and that the stimulation seems to diminish and to reach T-0 level at 1/10 and 1/7 dilution (FIG. 7B) around 48 and 72 hours for BIO-K-Plus™ supernatants (without milk product).

General Conclusion Following Obtained Results

In view of the obtained results in this part of the study, the lactic acid bacteria contained in the products BIO-K-Plus seem to secrete active molecules which have a potential of an antiangiogenic activity. Thus, these active molecules have the capacity of inhibiting the growth of new capillaries, which aids the progression of diverse sicknesses such as retinopathy, infantile haemangioma, rheumatoid arthritis, the psoriasis, the duodenal ulcers, the post-angioplasty restenosis and the tumour growth.

Effect Of Lactic Acid Bacteria On Cancer Cell Lines

Objective

Characterise the molecular mechanisms of BIO-K-Plus in various endothelial cell lines and human cancer cell lines.

Experimental Approach

A. In vitro characterization of antiangiogenic properties of BIO-K-Plus on endothelial cells lines of human umbilical veins (HUVEC).
 1. Effect on cell proliferation
 2. Effect on cell migratory potential
 3. Effect on capillary structure formation on Matrigel.
B. In vitro characterizations on anticancer properties of BIO-K-Plus on the proliferation of six tumour cell lines.
 1. MCF-7 (breast adenocarcinoma)
 2. Panc-1 (pancreas epitheloid carcinoma)
 3. PC-3 (prostate carcinoma)
 4. Daoy (brain medulloblastoma)
 5. U-87 (brain glioblastoma-astrocytoma)
 6. Jurkat (leukemia lymphocytes)

These studies will permit to better characterize and identify new molecular targets, modulated by BIO-K-Plus, endothelial cells and cancerous cells modulated by BIO-K-Plus.

1.1 Preparation of Study Material

In the present study, the inventors have characterized the supernatants action of irradiated lactic acid bacteria at 3 kGy (S3), 6 kGy (S6) and 9 kGy (S9). These supernatants have been obtained after two centrifugations (one at 6 000 g for 15 min at 4° C. and the other at 10 000 g for 20 min at 4° C.). They have then been filtered on two filters (on filter of 0.05 µm followed by a filter of 0.22 µm) to obtain bacteria free sterile supernatants and in order to be able to treat divers cells lines. Supernatants have been kept at −80° C. until use.

For those studies, the inventors have used a concentration of supernatants equivalent to $10^8$ bacteria, since it is at this concentration that the inhibitor effect is maximal.

Figure 8A:
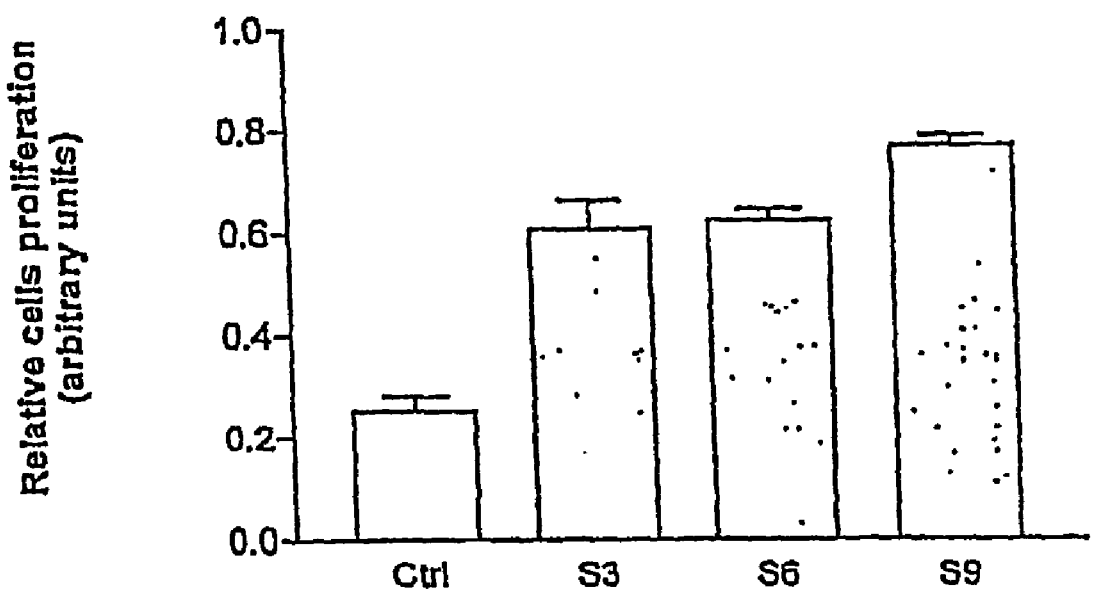
FIGS. 8A and 8B shows the effect of lactic bacteria supernatants on the proliferation of endothelial cells after 65 h treatment.
Figure 8B:
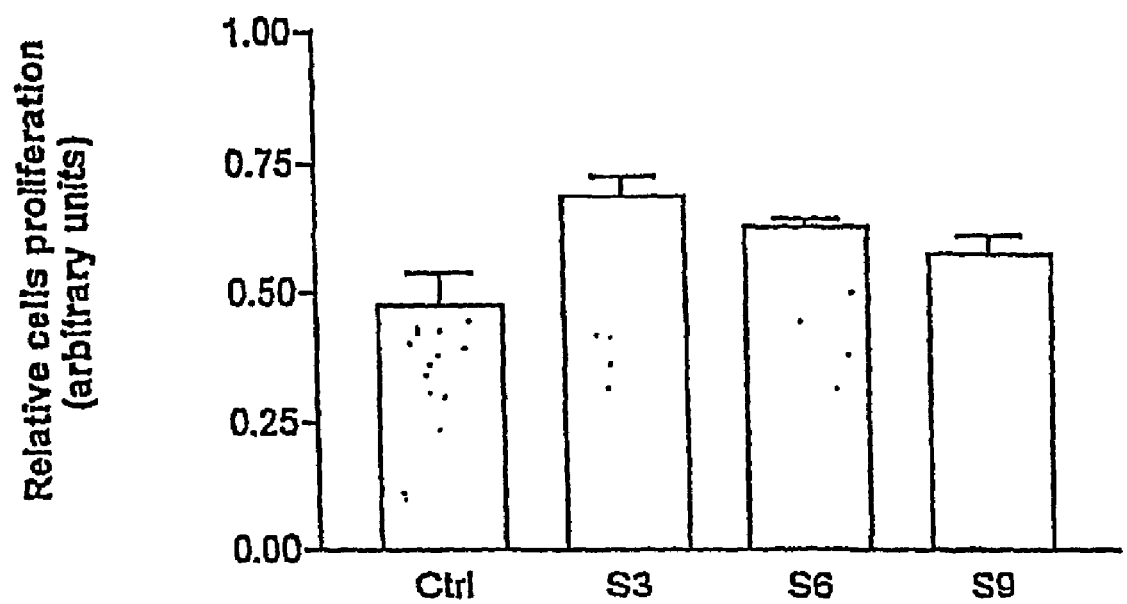
Figure 9:
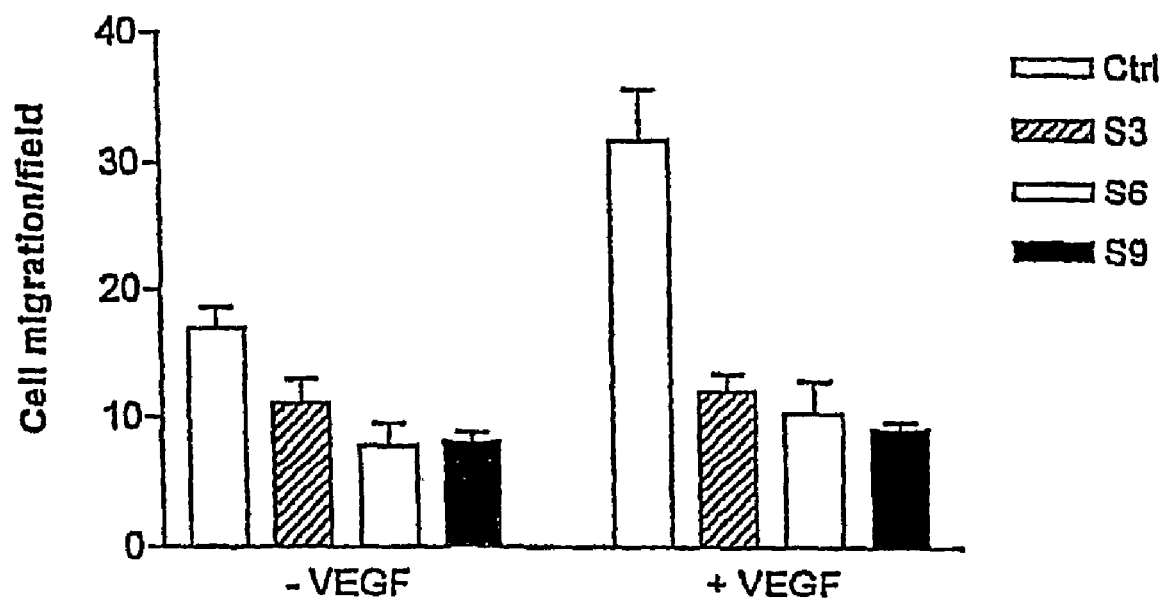
FIG. 9 shows the effect of lactic bacteria supernatants on the migration of endothelial cells.
Figure 10A:
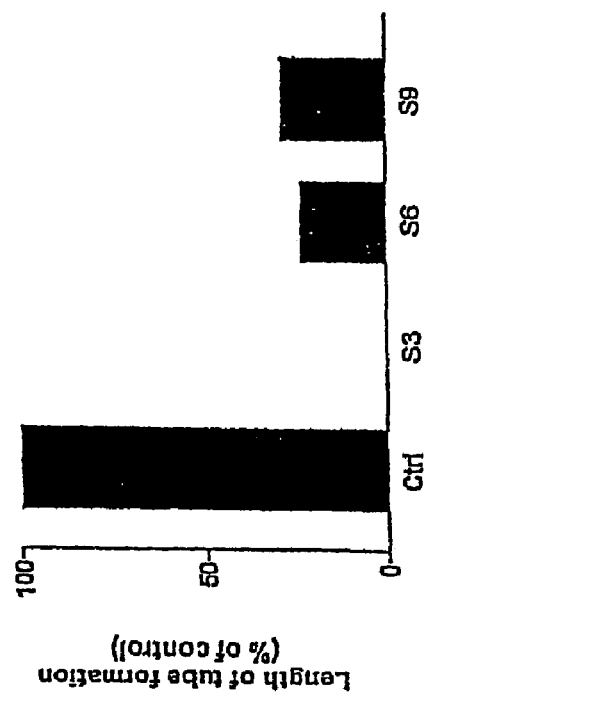
FIGS. 10A and 10B show the effect of the supernatants of the lactic bacteria on the tube formation by endothelial cells.
Figure 10A:
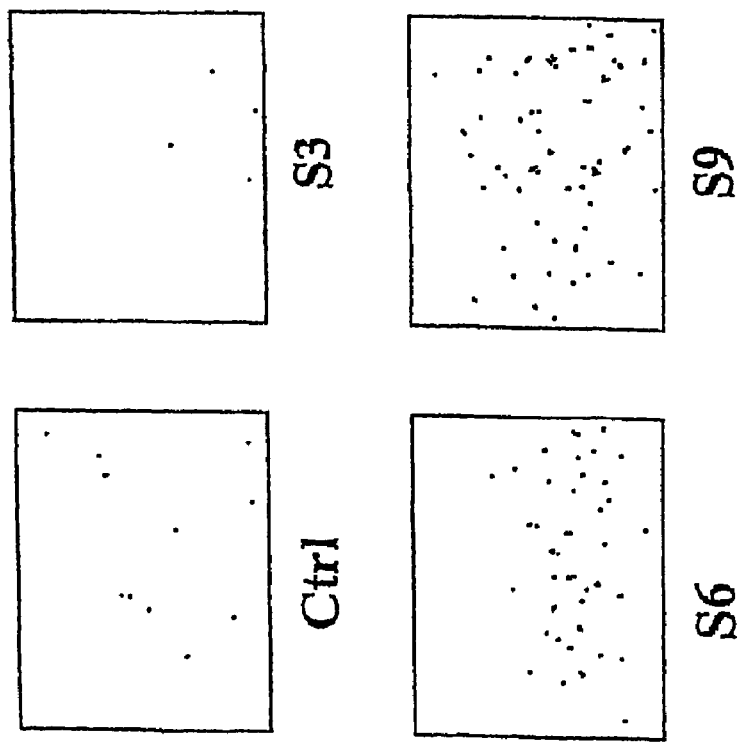
Figure 10B:
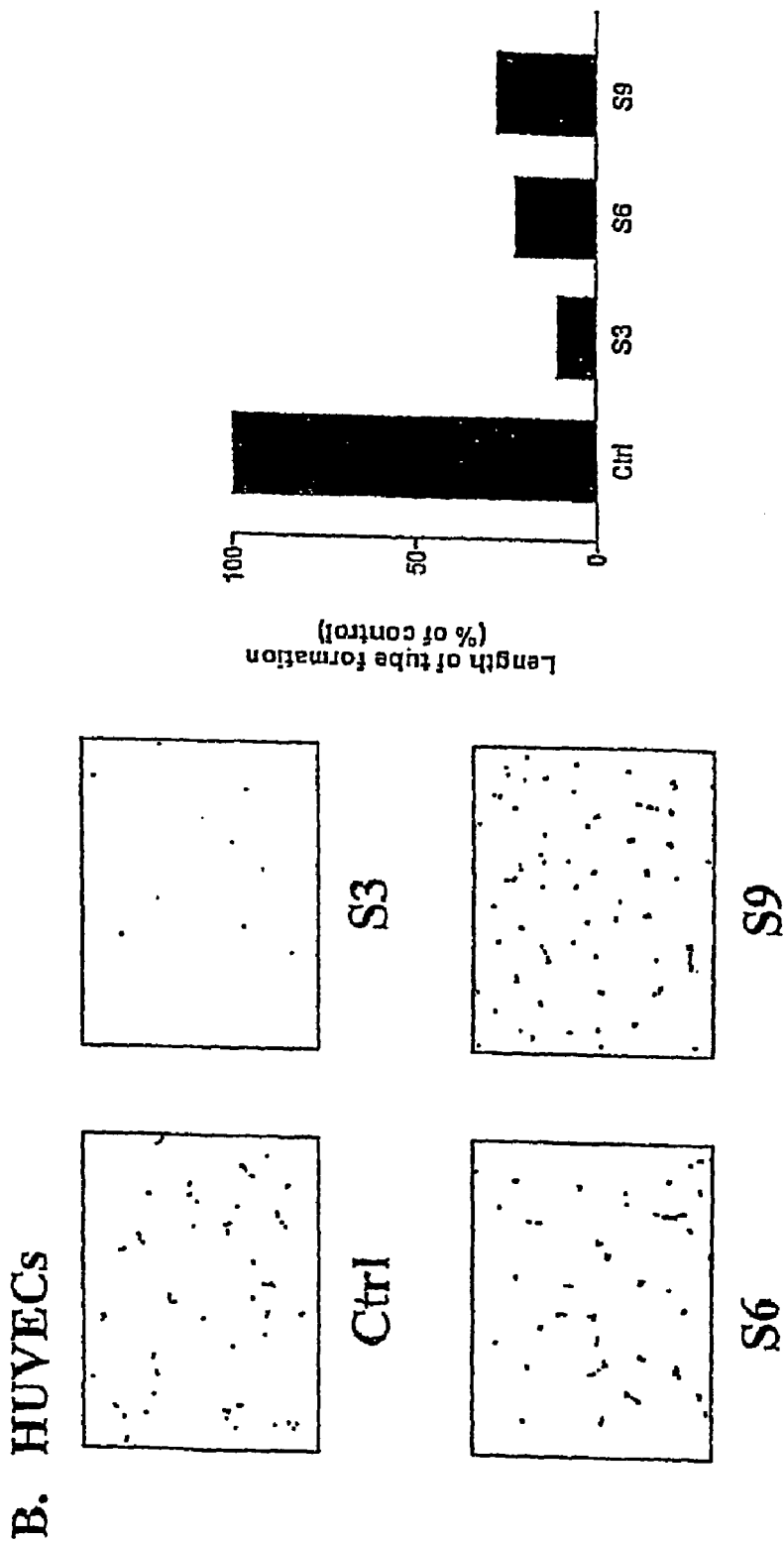
Figure 11A:
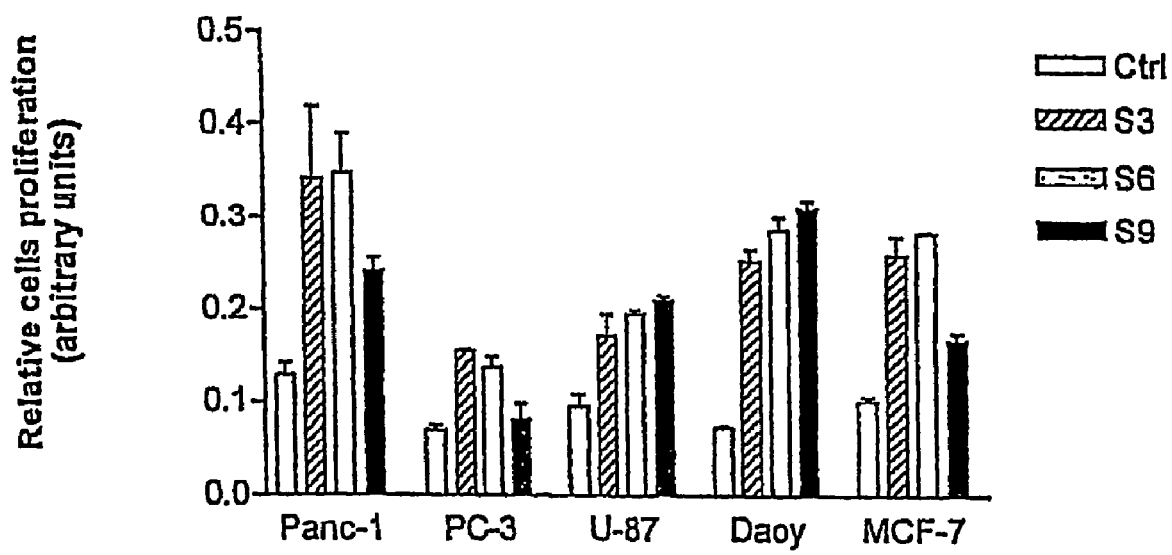
FIGS. 11A and 11B show the effect of lactic bacteria supernatants on the proliferation of tumoral cells after 65 h treatment.
Figure 11B:
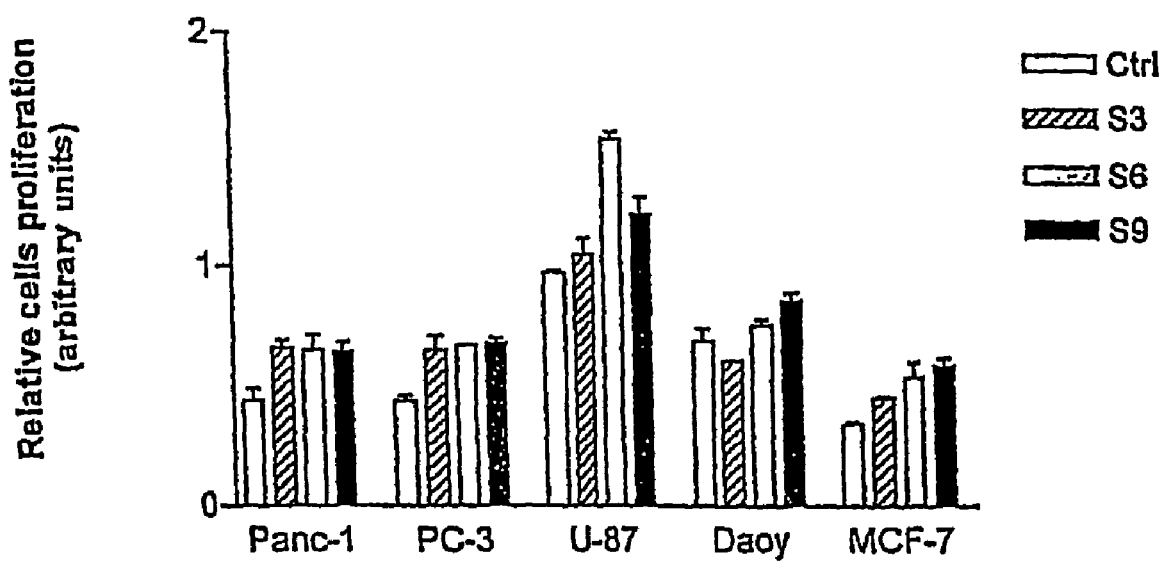
Figure 12:
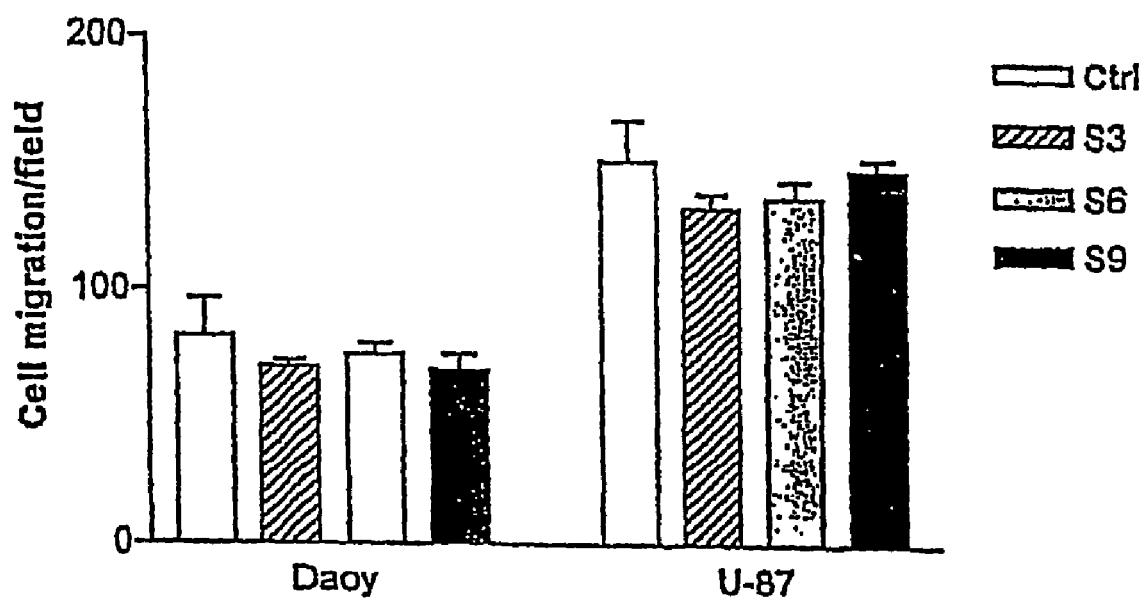
FIG. 12 shows the effect of lactic acid bacteria supernatants on the migration of tumoral cells.
Figure 13:
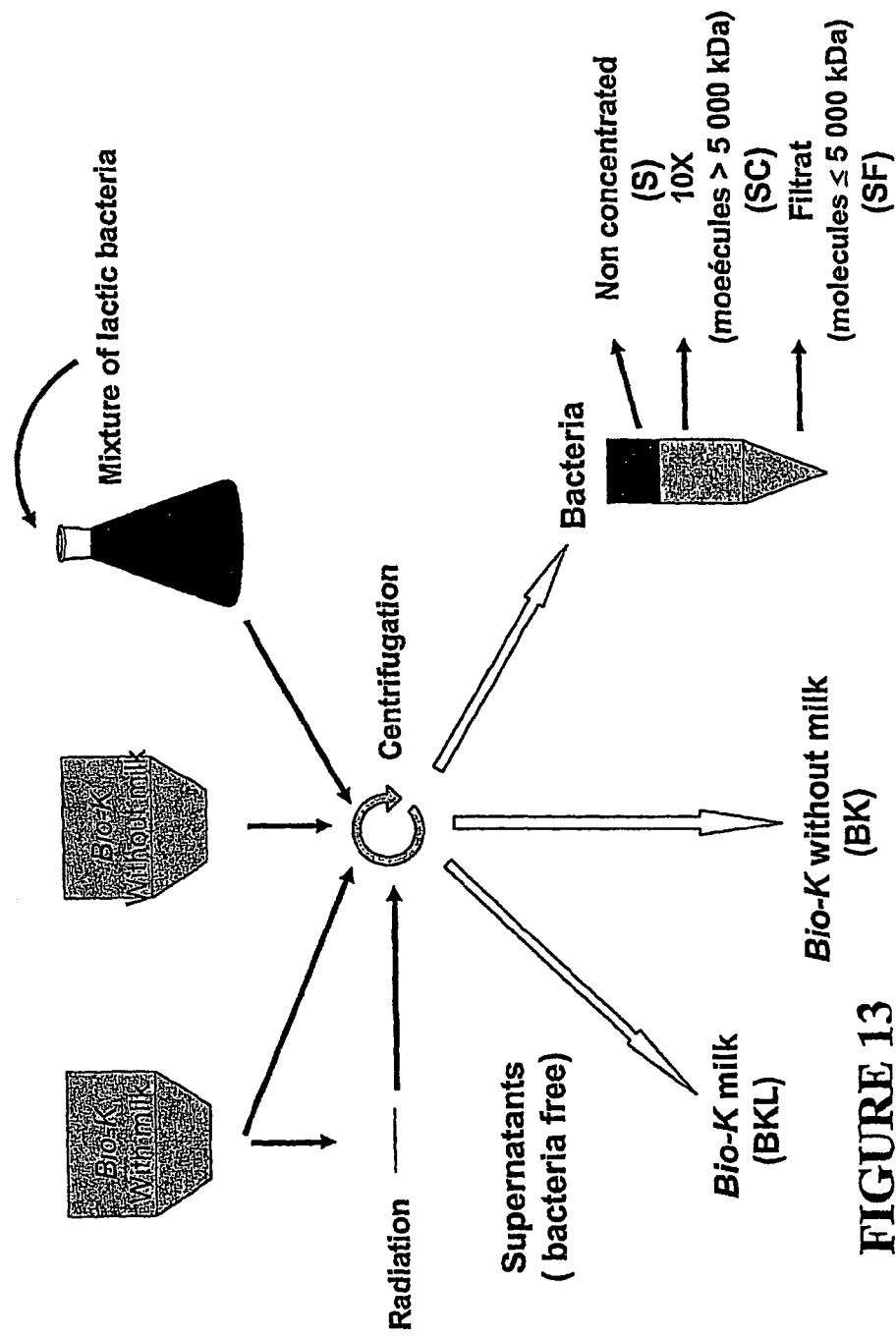
FIG. 13 shows the preparation of the different Bio-K Plus™ supernatants.
Figure 14:
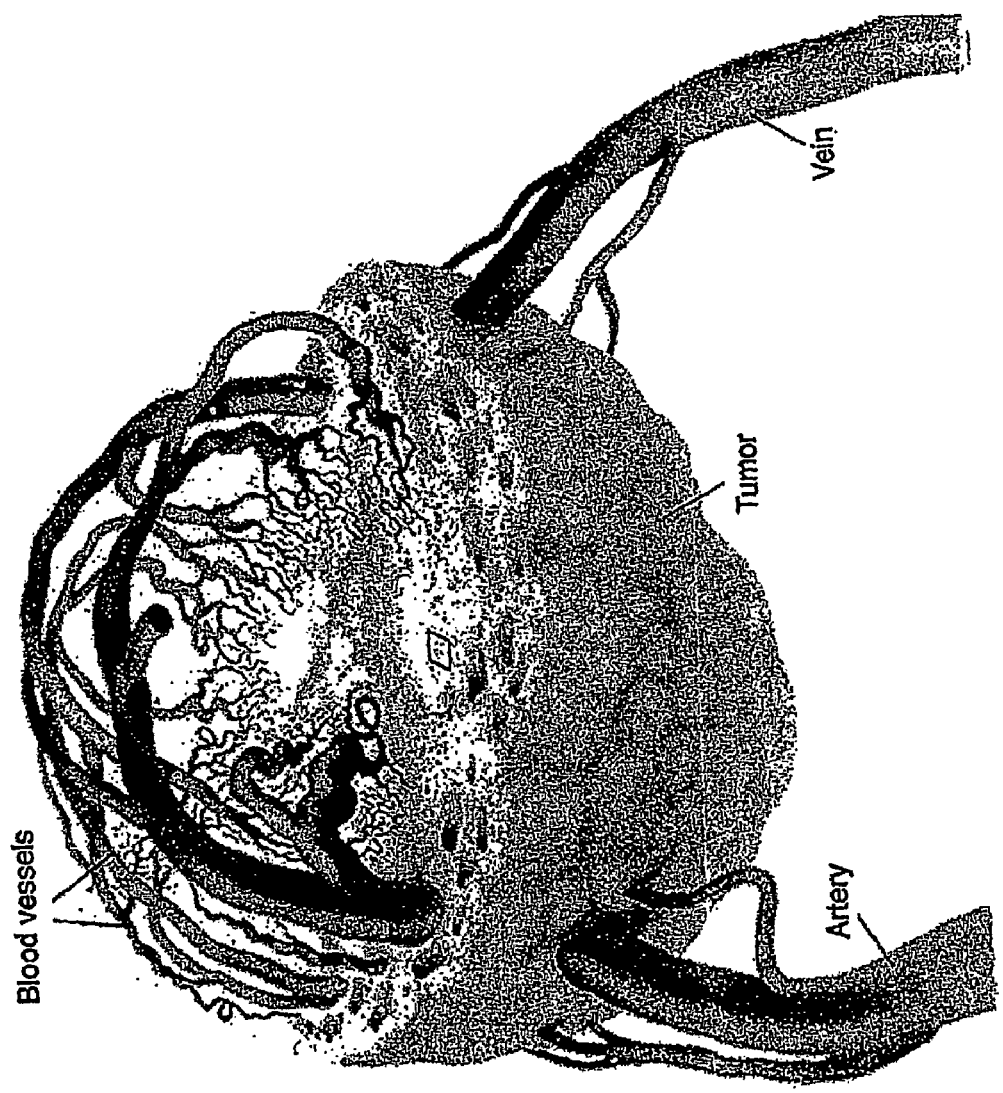
FIG. 14 shows a tumour and its blood vessels.
Figure 15:
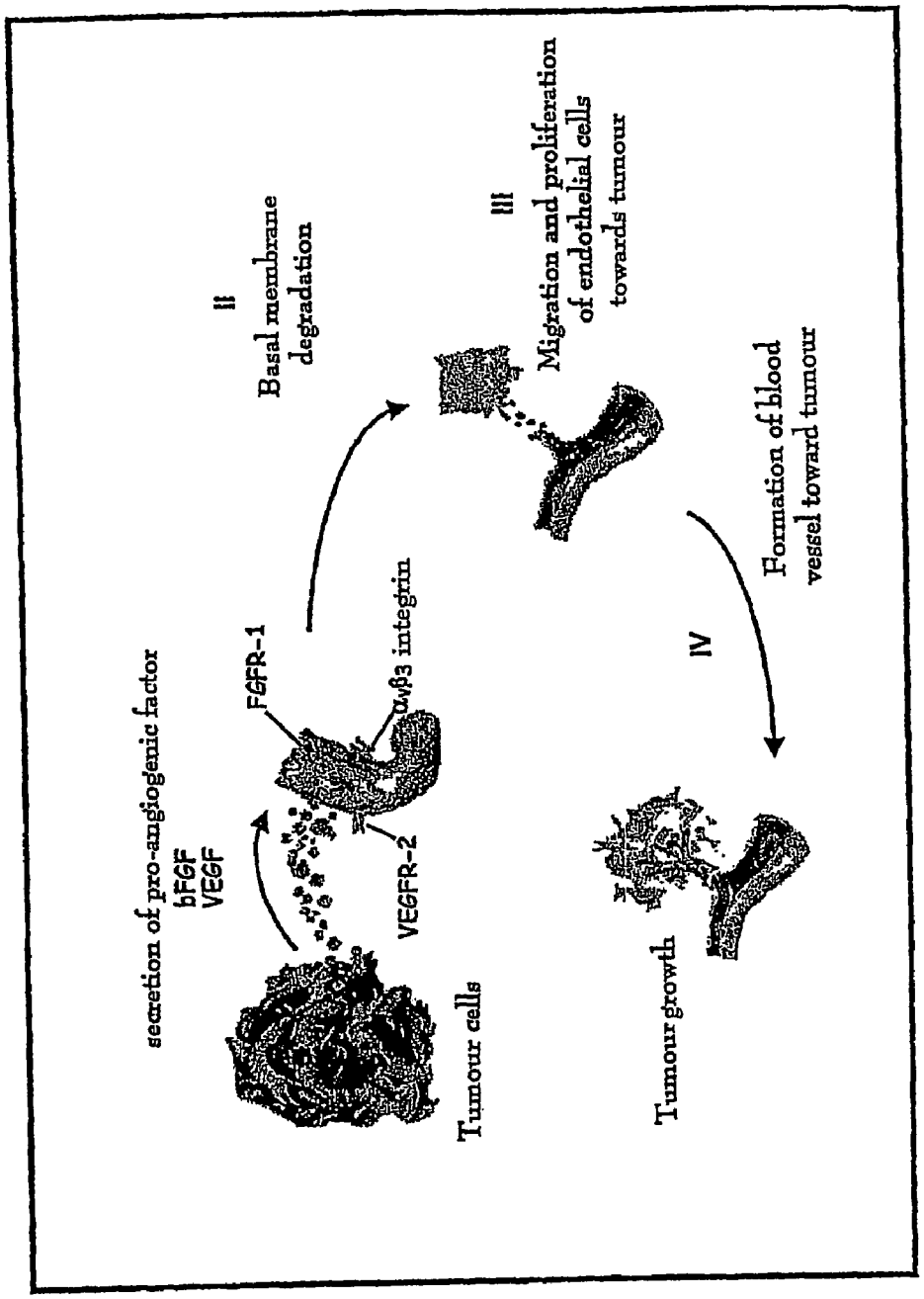
FIGS. 15 and 16 show tumoral angiogenesis.
Figure 16:
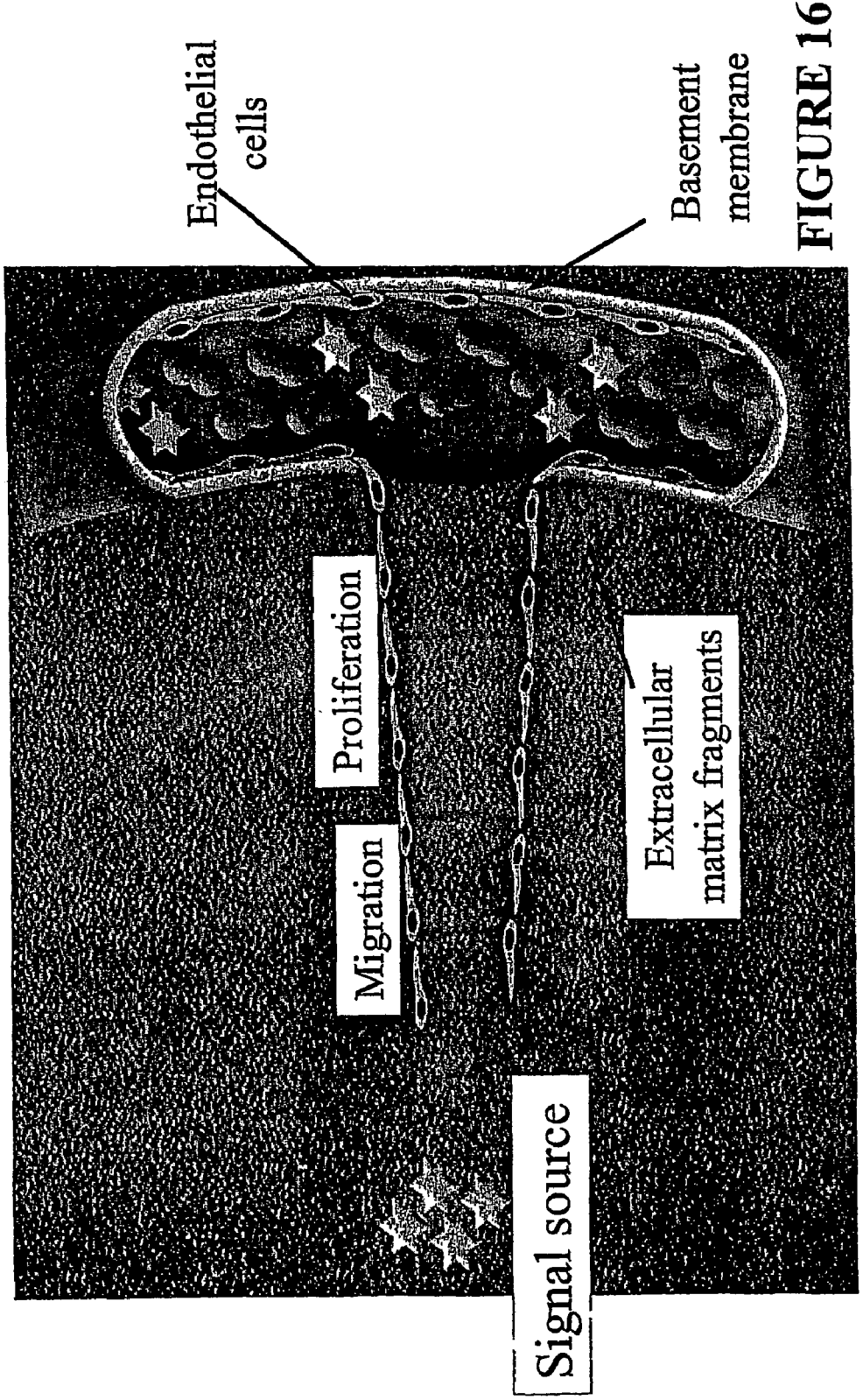
Figure 17:
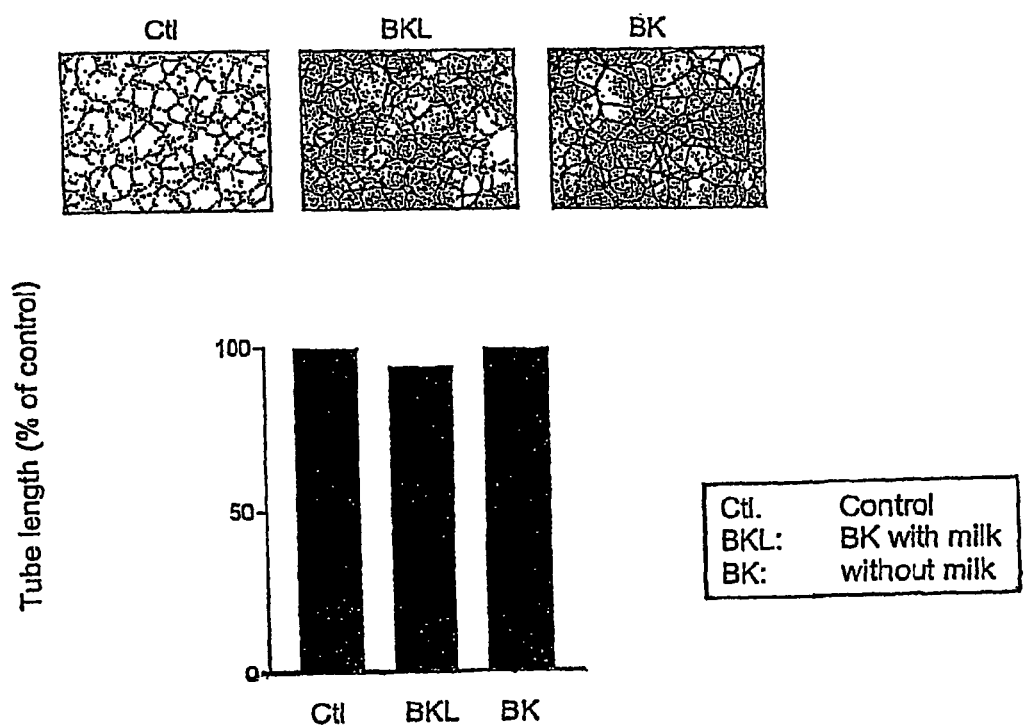
FIG. 17 shows the effect of different Bio-K Plus™ supernatants on the formation of capillary structures by endothelial cells (HUVEC).
Figure 18:
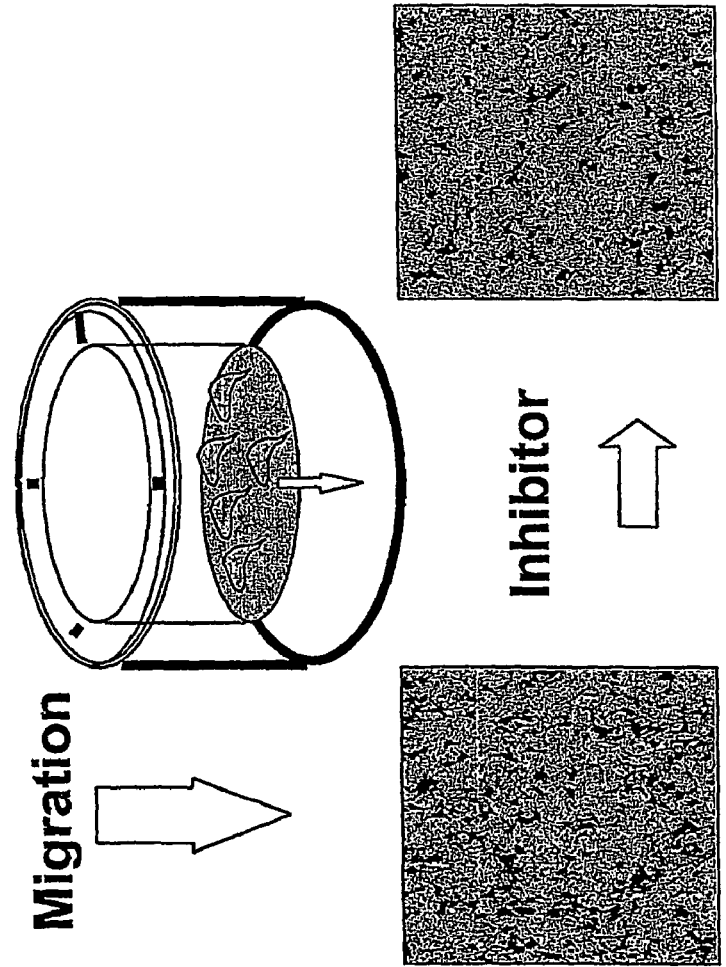
FIG. 18 shows the migration assay.
Figure 19:
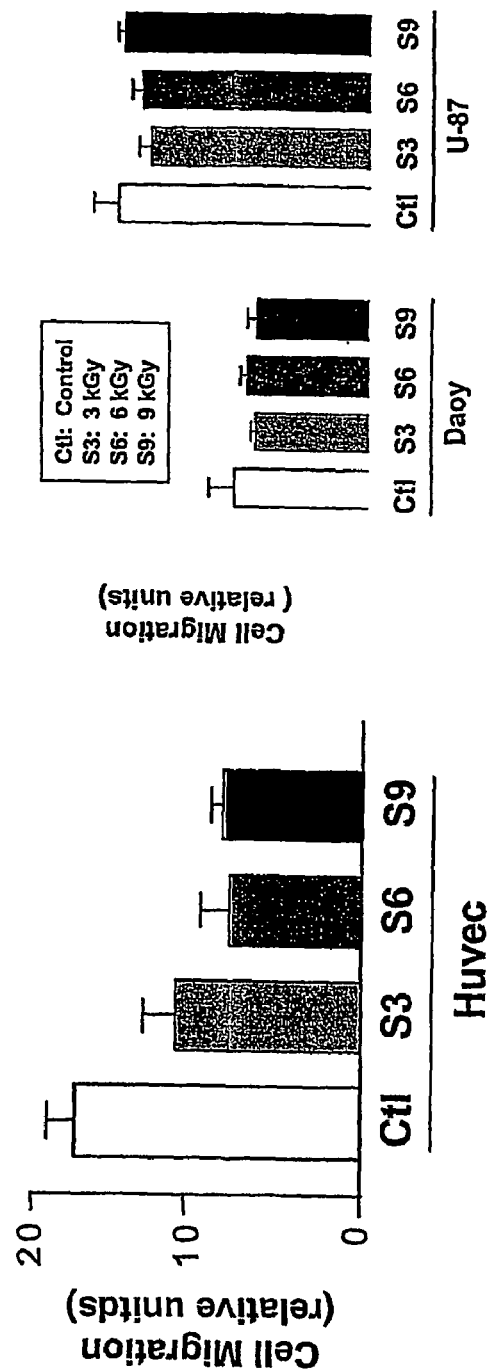
FIG. 19 shows the effect of Bio-K Plus™ supernatants on cell migration: inhibition of endothelial cells.
Figure 20:
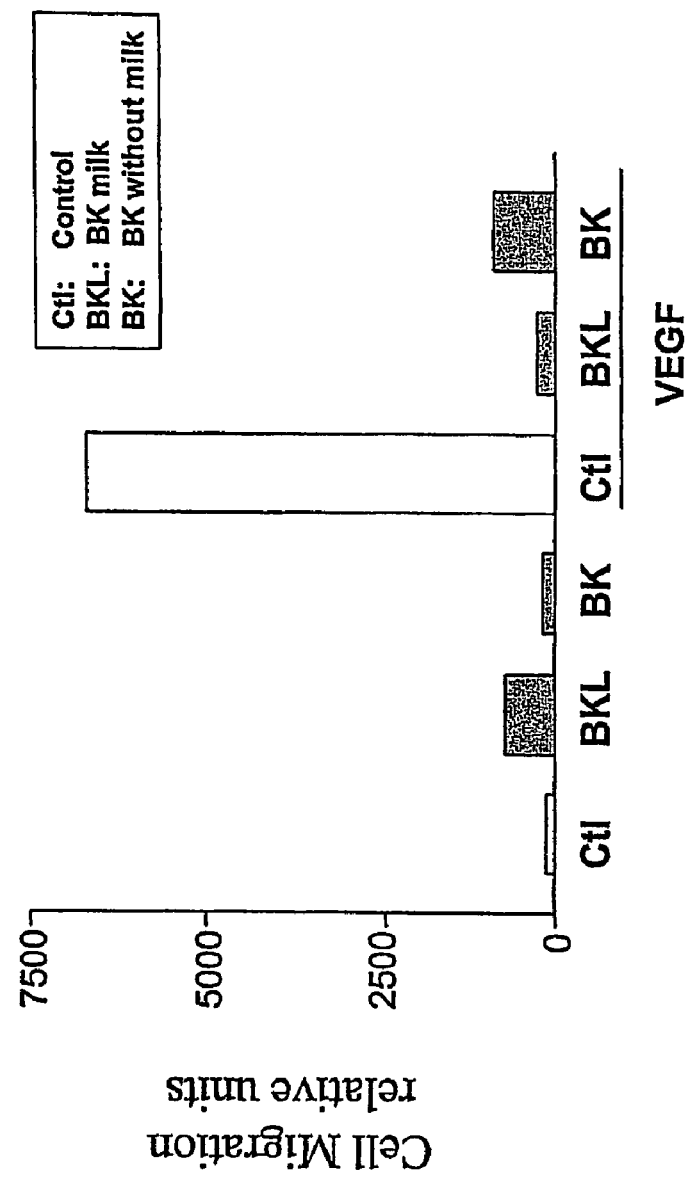
FIG. 20 shows the effect of Bio-K Plus™ supernatants on BAECs cell migration.
Figure 21:
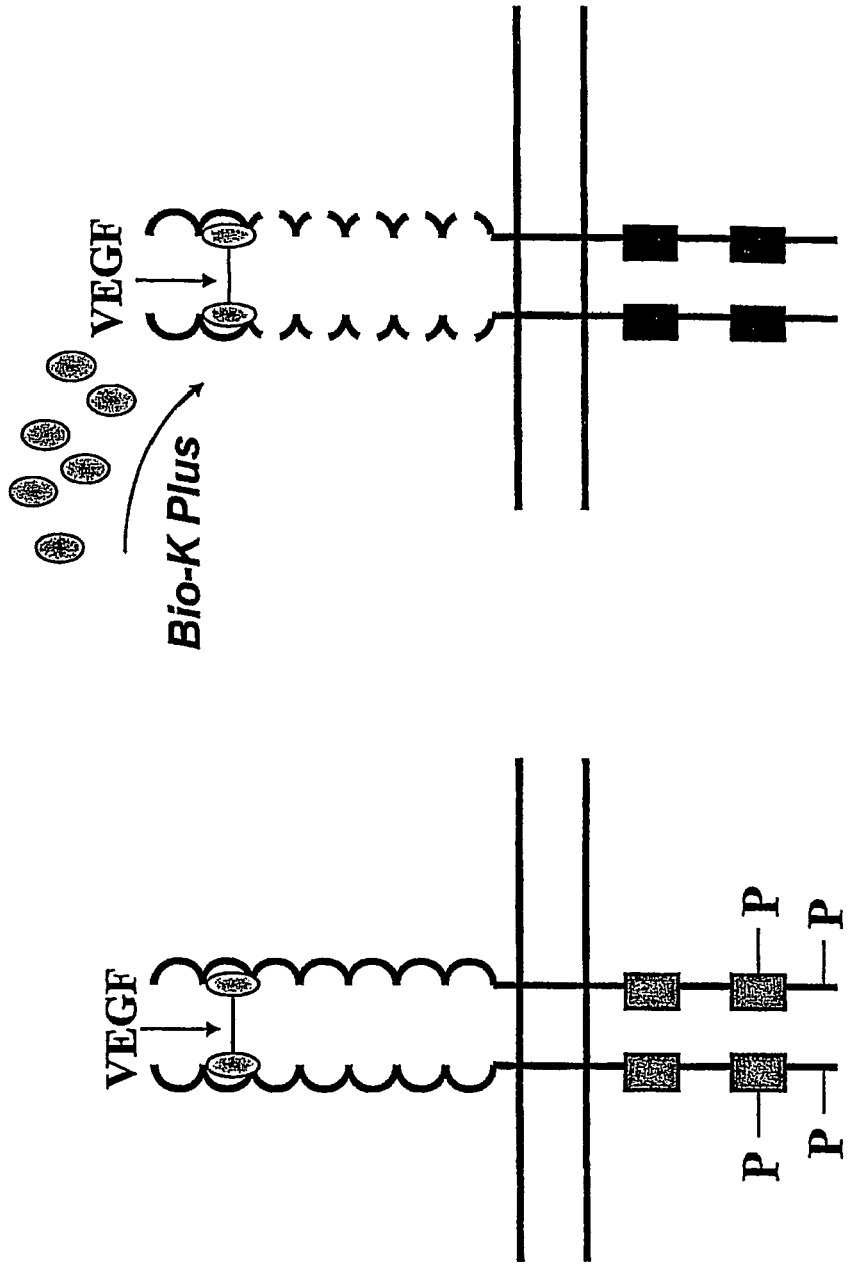
FIG. 21 shows receptor phosphorylation.
Figure 22:
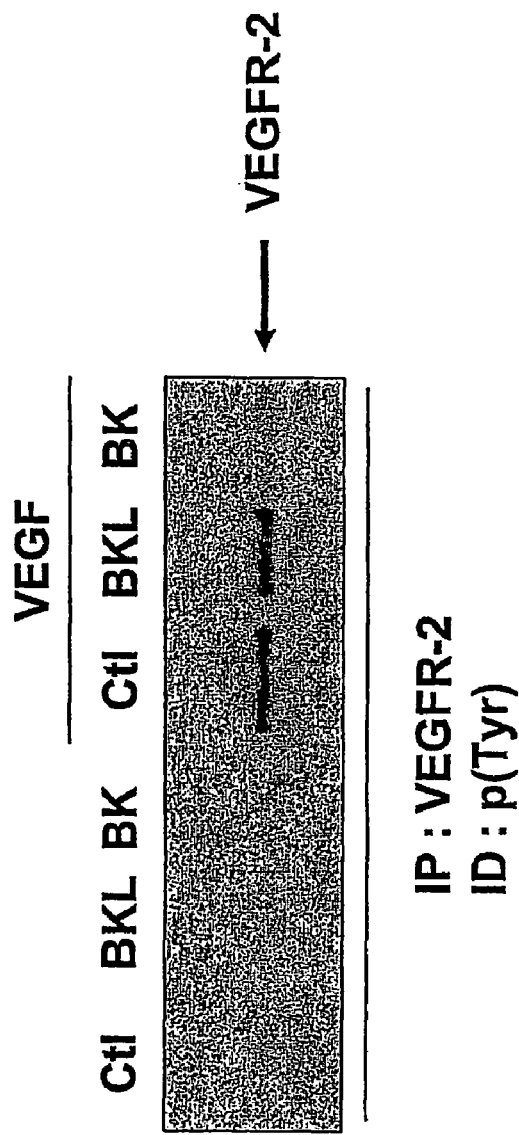
FIG. 22 shows the effect of Bio-K Plus™ supernatant on VEGFR-2 phosphorylation.
Figure 23:
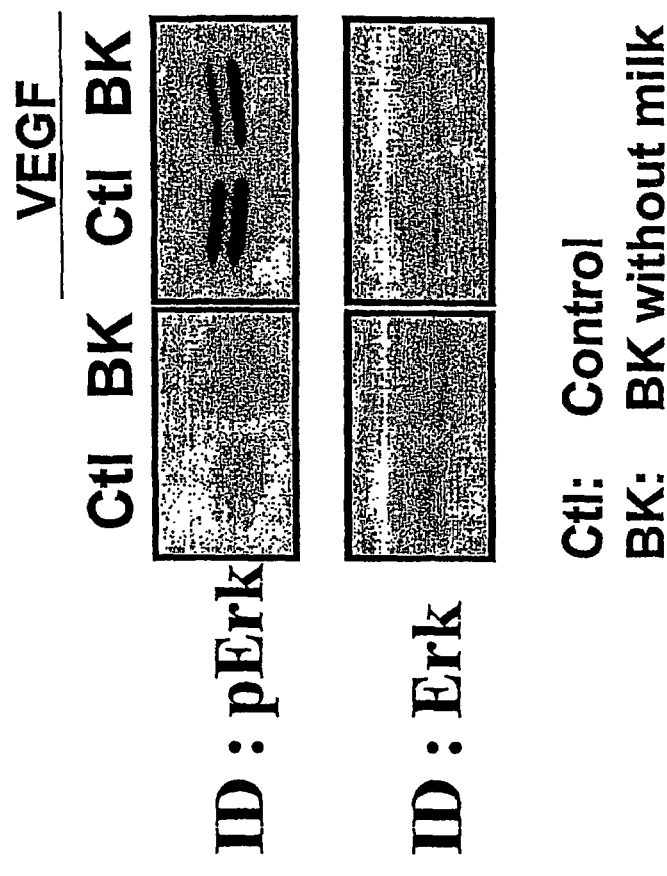
FIG. 23 shows the effect of Bio-K Plus™ supernatant phosphorylation of protein Erk by VEGF.
Figure 24:
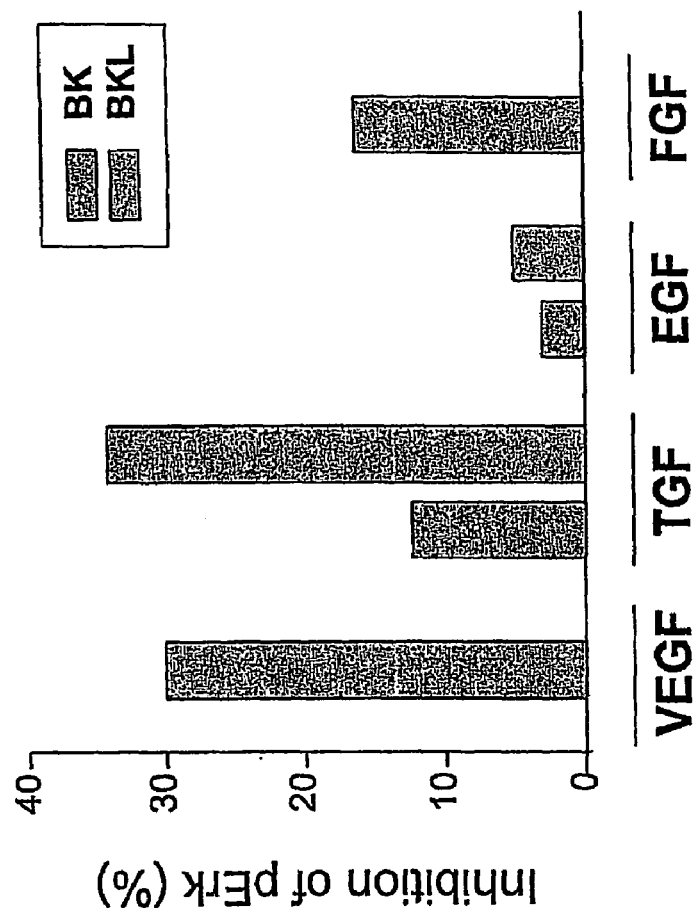
FIG. 24 shows the antagonist effect of Bio-K Plus™ supernatants on different receptors of growth factors.
Figure 25:
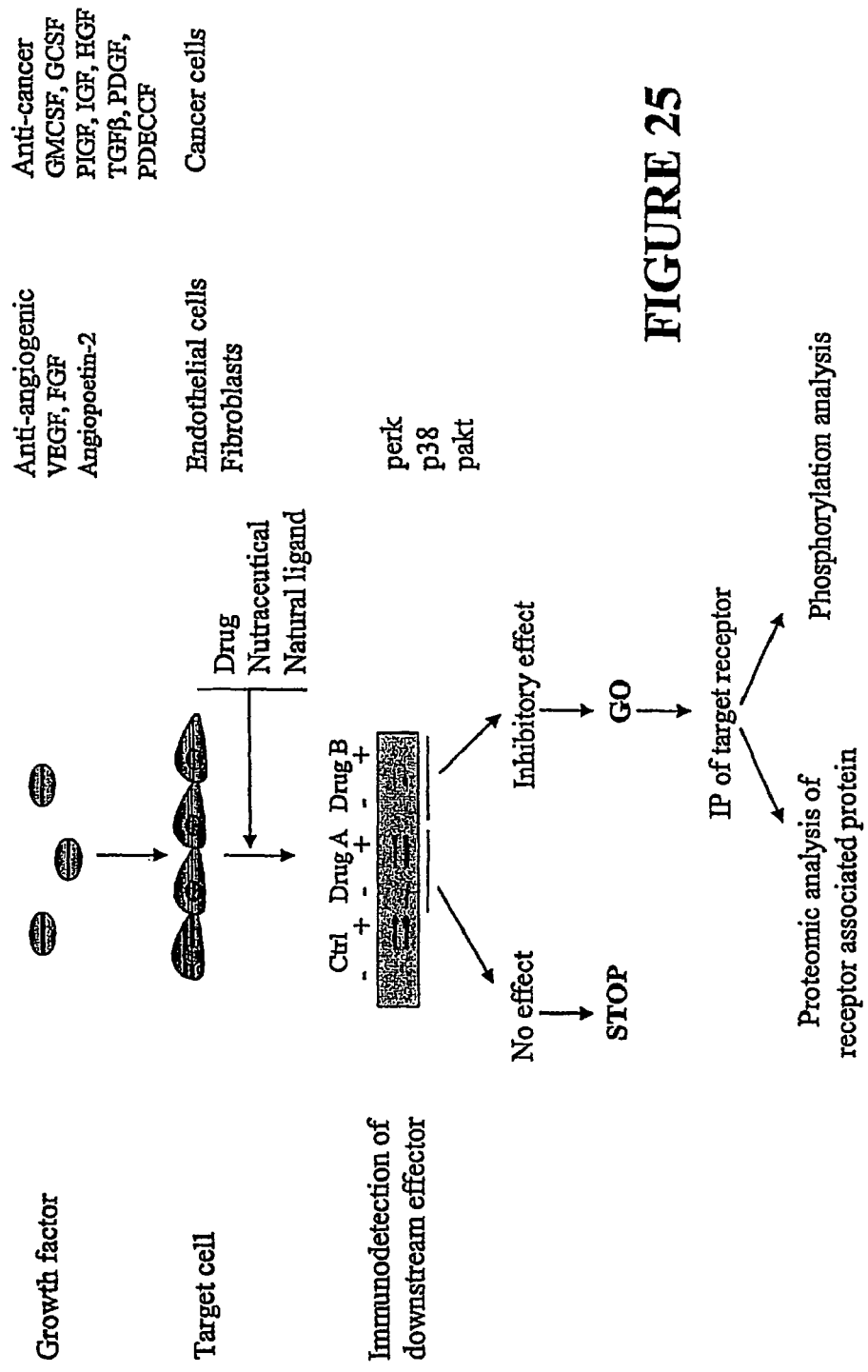
FIG. 25 shows high throughput screening of growth factor receptor inhibitors in cancer and angiogenesis.
Figure 26:
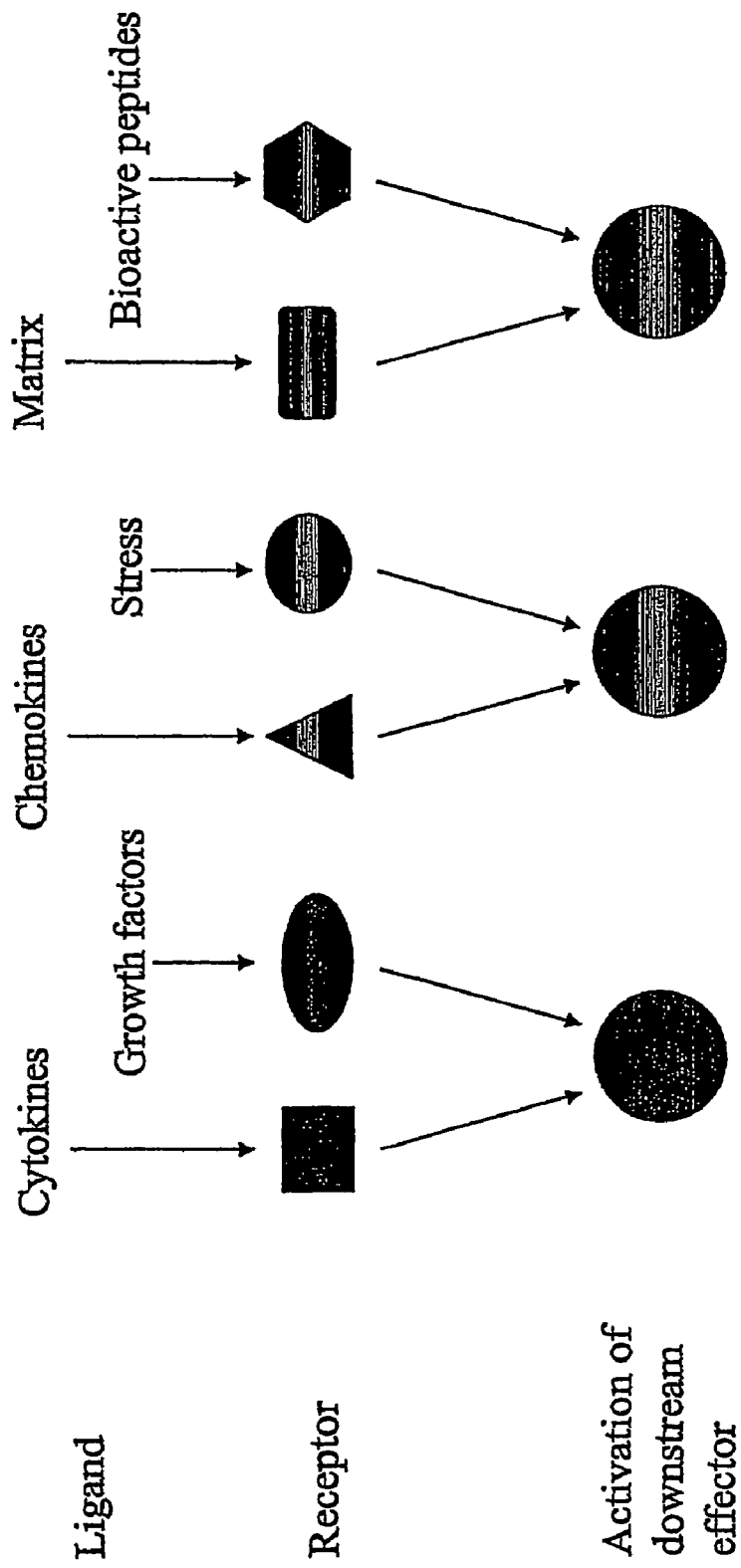
FIG. 26 shows molecular screening of receptor antagonists.

1.2 In Vitro Characterization of Antiangiogenic Properties of Bio-K-Plus on HUVECs The inventors have verified if bacterial supernatants have an effect on endothelial cells. The WST-1 technique, which measures mitochondrial activity of cells, has permitted the study of the cell proliferation of HUVECs. The supernatants did not seem to have an inhibitory effect on the cells proliferation (FIGS. 8 and 9; n=2). The inventors have then evaluated the migratory potential of cells in presence of bacterial supernatants and the results have been positive. The inventors have verified if supernatants inhibit the stimulation of HUVECs migration on gelatine induce by VEGF, the mitogen the most often associated with angiogenesis phenomena. The supernatants inhibit completely the migration by VEGF but also the basal level of migration at approximately 50% (FIG. 10B). The inhibitor effect of supernatants does not seem to be specific to VEGF. The assays of tube formation on Matrigel (in laminin rich matrix, reconstituting the basal membrane and which permits the endothelial cells differentiation in similar structures to capillary blood vessels) demonstrate that bacterial supernatants inhibit in a significant way the tube formation compared to a control in HUVECs (FIGS. 11A and 11B; n=2). These results indicate that bacterial supernatants contain molecules which have an antiangiogenic potential.

1.3 Conclusion

The inventors have demonstrated that the supernatants coming from lactic acid bacteria containing *Lactobacillus acidophilus* and *Lactobacillus casei* has an antiangiogenic activity.

The invention claimed is:

1. A method for treatment of an angiogenesis dependent disorder, the method comprising administering to a mammal an effective amount of a lactic composition comprising a mixture of bacterial strains selected from the group consisting of *Lactobacillus acidophilus* and *Lactobacillus casei*, and a whole broth of said mixture, wherein at least one *Lactobacillus acidophilus* strain in the mixture is I-1492 deposited at the CNCM and wherein the angiogenesis dependent disorder is selected from the group consisting of retinopathy, infantile haemangioma, rheumatoid arthritis, psoriasis, and post-angioplasty restenosis.

2. The method according to claim 1, wherein said mammal is a human being.

3. The method according to claim 1 or 2, wherein said administration is oral administration.

4. The method of claim 1, wherein the lactic composition further comprises fermented milk proteins or fermented soy proteins.

5. A method for inhibiting angiogenesis, the method comprising administering to a mammal having an angiogenesis dependent disorder selected from the group consisting of retinopathy, infantile haemangioma, rheumatoid arthritis, psoriasis, and post-angioplasty restenosis an effective amount of a lactic composition comprising a mixture of bacterial strains selected from the group consisting of *Lactobacillus acidophilus* and *Lactobacillus casei*, and a whole broth of said mixture, wherein at least one *Lactobacillus acidophilus* strain in the mixture is I-1492 deposited at the CNCM.

* * * * *

UNITED STATES PATENT AND TRADEMARK OFFICE
CERTIFICATE OF CORRECTION

| | | |
|---|---|---|
| PATENT NO. | : 7,862,809 B2 | Page 1 of 1 |
| APPLICATION NO. | : 10/595819 | |
| DATED | : January 4, 2011 | |
| INVENTOR(S) | : Beliveau et al. | |

It is certified that error appears in the above-identified patent and that said Letters Patent is hereby corrected as shown below:

On the Title page, under Item "(30) Foreign Application Priority Data" and after "Nov. 13, 2003," please delete "2448643" and insert therefor -- 2448843 --.

Signed and Sealed this
Twenty-second Day of November, 2011

David J. Kappos
*Director of the United States Patent and Trademark Office*